United States Patent
Yoshioka et al.

(10) Patent No.: US 9,974,456 B2
(45) Date of Patent: May 22, 2018

(54) CARDIAC POTENTIAL MEASURING DEVICE AND CARDIAC POTENTIAL MEASURING METHOD

(71) Applicant: Panasonic Intellectual Property Management Co., Ltd., Osaka (JP)

(72) Inventors: Mototaka Yoshioka, Osaka (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 370 days.

(21) Appl. No.: 14/743,930

(22) Filed: Jun. 18, 2015

(65) Prior Publication Data

US 2015/0374251 A1 Dec. 31, 2015

(30) Foreign Application Priority Data

Jun. 30, 2014 (JP) ................................. 2014-135283

(51) Int. Cl.
*A61B 5/04* (2006.01)
*A61B 5/00* (2006.01)
*A61B 5/0408* (2006.01)
*A61B 5/0428* (2006.01)

(52) U.S. Cl.
CPC ........ *A61B 5/04011* (2013.01); *A61B 5/0428* (2013.01); *A61B 5/04085* (2013.01); *A61B 5/0006* (2013.01); *A61B 5/6804* (2013.01); *A61B 5/6838* (2013.01); *A61B 5/742* (2013.01)

(58) Field of Classification Search
None
See application file for complete search history.

(56) References Cited

U.S. PATENT DOCUMENTS 6,282,440 B1  8/2001  Brodnick et al.

FOREIGN PATENT DOCUMENTS

JP  2001-204701  7/2001
JP  2005-287849  10/2005

*Primary Examiner* — Brian T Gedeon
(74) *Attorney, Agent, or Firm* — McDermott Will & Emery LLP

(57) ABSTRACT

A cardiac potential measuring device comprising: a first electrode and a second electrode; a potential difference acquisition circuitry that acquires a potential difference between the first electrode and the second electrode as cardiac potential; an attachment direction detector that detects an attachment direction that is a direction of a virtual line that connects the first electrode and the second electrode attached to the body of the user; and an attachment direction calculator that calculates and outputs a preferred attachment direction in which the potential difference larger than any one of a first potential difference and a second potential difference is generated.

8 Claims, 31 Drawing Sheets

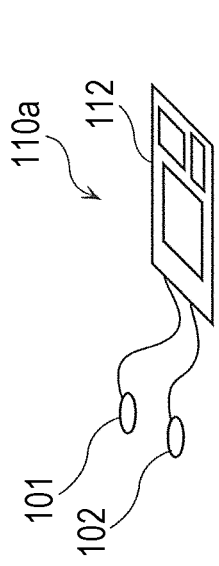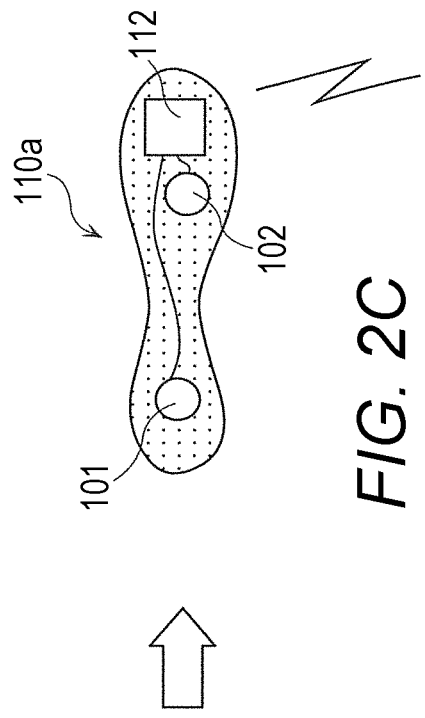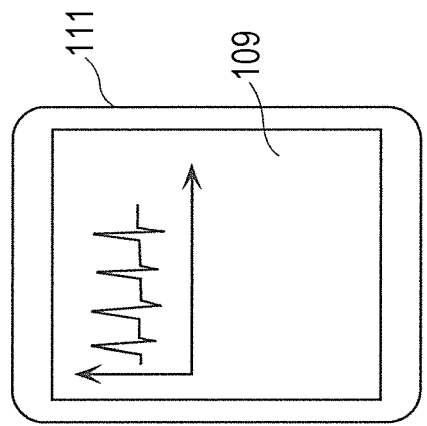

FIG. 9

| ATTACHMENT DIRECTION (G) | POTENTIAL DIFFERENCE ($\mu$V) |
|---|---|
| X=0, Y=0, Z=−1 | 85 |
| X=−1, Y=0, Z=0 | 50 |
| ⋮ | ⋮ |
|  |  |

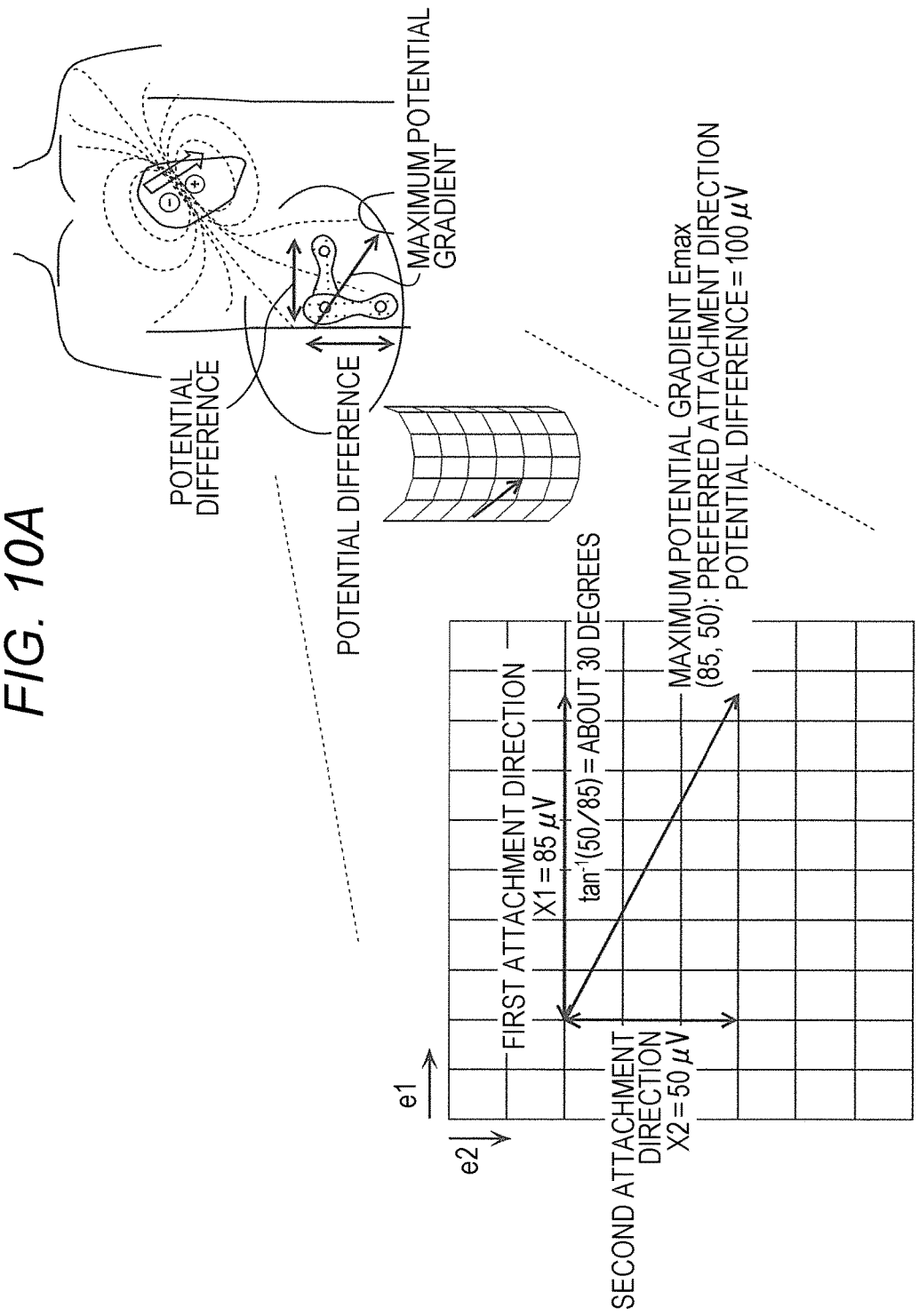

| ATTACHMENT DIRECTION (G) | POTENTIAL DIFFERENCE (μV) |
|---|---|
| X = 0, Y = 0, Z = −1 | 85 |
| X = −1, Y = 0, Z = 0 | 50 |
| MaxGradient (85, 50) | 100 |
| | |

CARDIAC POTENTIAL MEASURING DEVICE AND CARDIAC POTENTIAL MEASURING METHOD

BACKGROUND

1. Field of the Invention

The present disclosure relates to a device for measuring cardiac potential, and in particular to a device for measuring cardiac potential by using at least two electrode units.

2. Description of the Related Art

A cardiac potential measuring device disclosed in Patent Literature 1 determines whether placement of electrodes is correct. A cardiac potential measuring device used for medical treatment or diagnosis needs accurate placement of electrodes on a body surface of a user. For example, electrodes are placed at standard positions used in a limb-lead method made of four leads placed on both wrists and both ankles, or in a standard 12-lead method that induces 12 kinds of waveforms by combining limb leads and chest leads made of electrodes placed on predetermined positions on a chest. The cardiac potential measuring device disclosed in Patent Literature 1 determines whether the plurality of electrodes are placed at standard positions. Specifically, the cardiac potential measuring device uses potential obtained from the plurality of electrodes to calculate a vector of potential measured at each electrode as a covariance matrix, and to calculate an eigenvalue matrix. The eigenvalue included in the obtained eigenvalue matrix is compared with a previously accumulated value in correct electrode placement to determine whether the electrodes have been placed correctly.

CITATION LIST

Patent Literatures

PTL 1: Japanese Patent No. 4,733,262
PTL 2: Unexamined Japanese Patent Publication No. 2005-287849

However, the conventional technique disclosed in Patent Literature 1 determines whether the electrodes are correctly placed at the standard positions prescribed by the limb-lead method or standard 12-lead method, and does not take into consideration placement of the electrodes at positions other than the standard positions. The limb-lead method or standard 12-lead method needs placement of the electrodes in a wide area of the body including both wrists, both legs, and the chest. Therefore, it is difficult for general users who are not specialists in cardiac potential measurement to measure cardiac potential simply in daily life.

As a technique for detecting electrocardiographic waveforms accurately, another proposed technique detects the electrocardiographic waveforms induced on a portion on which electrodes are not attached (for example, see Patent Literature 2). However, the technique described in Patent Literature 2 also measures cardiac potential with the electrodes placed at the above-mentioned standard positions, and does not take into consideration general users measuring cardiac potential simply in daily life.

SUMMARY

The cardiac potential measuring device according to one aspect of the present disclosure allows the users to measure cardiac potential simply in daily life.

In order to achieve the above purposes, a cardiac potential measuring device according to one aspect of the present disclosure includes: a first electrode and a second electrode unit to be attached to a body; an attachment direction detector configured to detect an attachment direction that is a direction of a virtual line that connects the first electrode and the second electrode unit attached to the body; a potential difference acquisition unit configured to acquire a potential difference between the first electrode unit and the second electrode unit as cardiac potential; an attachment direction calculator configured to calculate and output a preferred attachment direction that is an attachment direction in which the potential difference larger than any one of a first potential difference and a second potential difference is generated, based on: (1) the first potential difference that is the potential difference acquired by the potential difference acquisition unit in a case where the first electrode unit and the second electrode unit are attached to the body in a first attachment state; (2) the second potential difference that is the potential difference acquired by the potential difference acquisition unit in a case where the first electrode and the second electrode unit are attached to the body in a second attachment state; and (3) a first attachment direction that is the attachment direction detected by the attachment direction detector in the first attachment state, and a second attachment direction that is the attachment direction detected by the attachment direction detector in the second attachment state, or an angle made by the first attachment direction and the second attachment direction.

These general or specific aspects may be implemented by a system, a method, an integrated circuit, a computer program, or a computer-readable recording medium such as a CD-ROM, and may be implemented by an arbitrary combination of a system, a method, an integrated circuit, a computer program, and a recording medium.

The cardiac potential measuring device according to one aspect of the present disclosure is capable of measuring cardiac potential simply while the user is having daily life.

BRIEF DESCRIPTION OF DRAWINGS

FIGS. 2A to 2C are external appearance diagrams of the cardiac potential measuring system according to the first exemplary embodiment;

FIG. 9 is a diagram illustrating an example of information accumulated in an accumulator according to the first exemplary embodiment;

FIG. 10A is a diagram illustrating an example of calculation of a preferred attachment direction according to the first exemplary embodiment;

DETAILED DESCRIPTION

Figure 1:
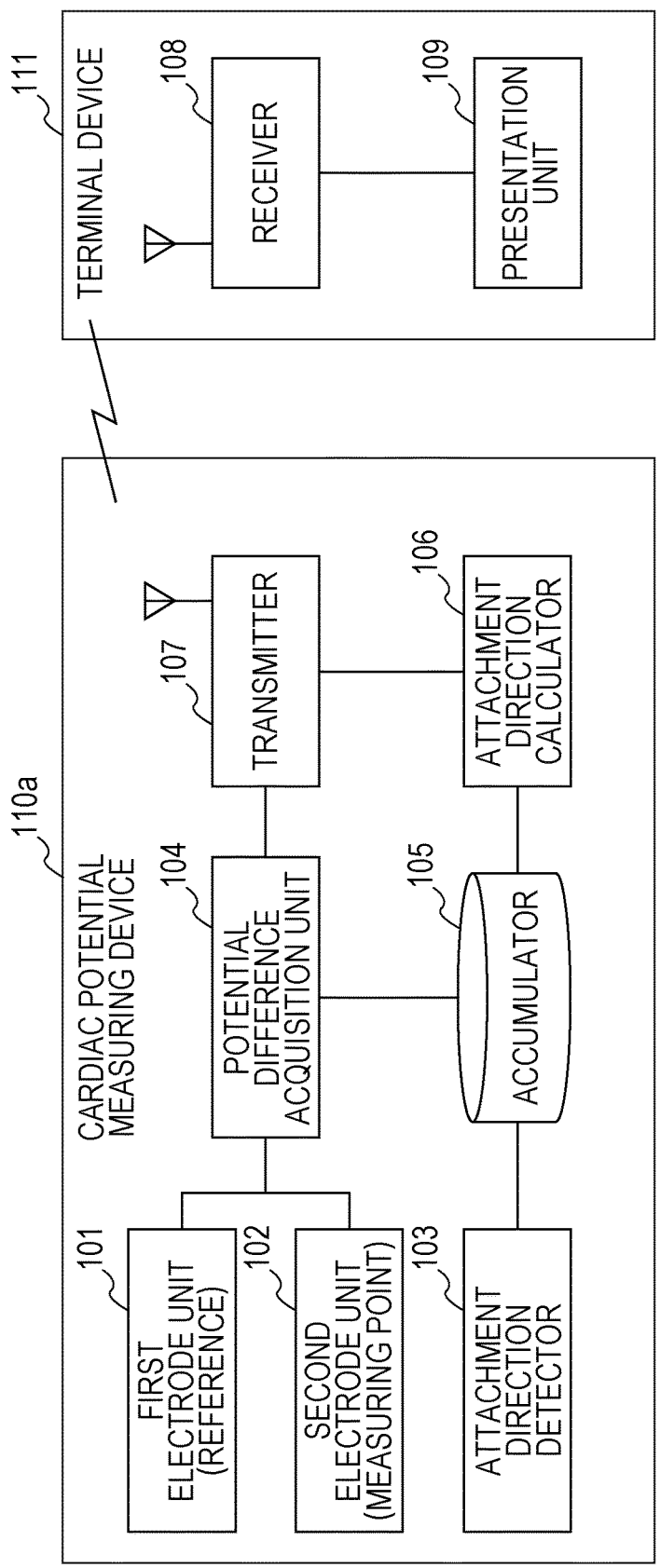
FIG. 1 is a block diagram illustrating a configuration of a cardiac potential measuring system according to a first exemplary embodiment.

A cardiac potential measuring device comprising: a first electrode and a second electrode; a potential difference acquisition circuitry that acquires a potential difference between the first electrode and the second electrode as cardiac potential; an attachment direction detector that detects an attachment direction that is a direction of a virtual line that connects the first electrode and the second electrode attached to the body of the user; and an attachment direction calculator that calculates and outputs a preferred attachment direction in which the potential difference larger than any one of a first potential difference and a second potential difference is generated, based on: (a) the first potential difference acquired by the potential difference acquisition circuitry when the first electrode and the second electrode are attached to the body of the user in a first attachment state; (b) the second potential difference acquired by the potential difference acquisition circuitry when the first electrode and the second electrode are attached to the body of the user in a second attachment state; and (c) a first attachment direction detected in the first attachment state, and a second attachment direction in the second attachment state, or an angle made by the first attachment direction and the second attachment direction.

Accordingly, the cardiac potential measuring device calculates and outputs the preferred attachment direction in which the potential difference larger than any one of the first potential difference and the second potential difference is generated, based on (1) the first potential difference, (2) the second potential difference, and (3) the first attachment direction and the second attachment direction or the angle made by these directions. Therefore, even general users who are not specialists in cardiac potential measurement can know more preferable attachment direction by attaching the first electrode and the second electrode unit in the two attachment states, which enables the general users to measure cardiac potential simply while leading daily life.

Here, the attachment direction calculator may calculate a direction in which a maximum potential gradient is generated from a vector specified by the first potential difference and the first attachment direction, and a vector specified by the second potential difference and the second attachment direction, and may calculate the direction as the preferred attachment direction.

This allows calculation of the preferred attachment direction in which the maximum potential gradient is generated based on the vector obtained in the first attachment state and the vector obtained in the second attachment state. Thus, the attachment direction in which large potential difference is generated is securely calculated as the preferred attachment direction.

In addition, the cardiac potential measuring device may further include a presentation unit configured to present the preferred attachment direction that is calculated by the attachment direction calculator.

This causes the presentation unit to present the preferred attachment direction, and thus allows the users to know the preferred attachment direction visually.

In addition, the attachment direction calculator may calculate the potential difference in the preferred attachment direction, in addition to calculation of a direction in which a maximum potential gradient is generated as the preferred attachment direction, based on: (1) the first potential difference; (2) the second potential difference; and (3) the first attachment direction and the second attachment direction, or the angle. The cardiac potential measuring device may further include an attachment direction check unit configured to compare the potential difference acquired by the potential difference acquisition unit with the potential difference in the preferred attachment direction, and based on a result of comparison, to present an image urging reattachment in the preferred attachment direction via the presentation unit.

This urges reattachment in the preferred attachment direction via the presentation unit in a case where a difference is large between the potential difference measured and the potential difference in the known preferred attachment direction. Thus, this can avoid low-precision cardiac potential measurement caused by an inadequate attachment direction.

In addition, the cardiac potential measuring device may further include an attachment position check unit configured to determine whether a position of the first electrode unit in the first attachment state and a position of the first electrode in the second attachment state are within a predetermined range. The attachment direction calculator may calculate and output the preferred attachment direction in a case where the attachment position check unit determines that the position of the first electrode in the first attachment state and the position of the first electrode unit in the second attachment state are within the predetermined range.

This causes the preferred attachment direction to be calculated, for example, only when the position of the first electrode that serves as a reference electrode is not deviated significantly between the first attachment state and the second attachment state. Thus, this can avoid a problem that the low-precision preferred attachment direction is presented.

In addition, the cardiac potential measuring device may further include: a plate for holding at least one of the first electrode and the second electrode unit; a locking piece to be locked to the body or to clothes that wrap the body; and a support for holding the plate and the locking piece spaced by a certain distance and for holding the plate pivotably in a plane of the plate.

This causes the cardiac potential measuring device to have clip structure including the plate, the locking piece, and the support, and the plate holding the electrode units pivots. Accordingly, users can hold the cardiac potential measuring device at a desired position on the body by nipping clothes or the like with the locking piece and the plate, and can measure cardiac potential in arbitrary directions.

In addition, the plate may hold the first electrode and the second electrode unit so that the first electrode and the second electrode unit may be spaced by a certain distance in plan view of the plate.

Since the plate holds two electrode units (the first electrode and the second electrode unit) accordingly, users can change the attachment direction simply by only rotating the plate.

In addition, the plate may hold a third electrode unit to be attached to the body, and the first electrode, the second electrode unit, and the third electrode unit may be held on the plate so that the direction of the virtual line that connects the first electrode and the second electrode unit may be orthogonal to a direction of a virtual line that connects the first electrode and the third electrode unit.

This causes the three electrode units (the first electrode, the second electrode unit, and the third electrode unit) to measure the potential difference in each of the two attachment directions orthogonal to each other. Accordingly, the preferred attachment direction is calculated highly precisely through work to attach the plate to the body only once.

In addition, in order to achieve the above objects, the cardiac potential measuring device according to one aspect of the present disclosure includes: a first electrode and a second electrode unit to be attached to a body; a plate for holding at least one of the first electrode and the second electrode unit; a locking piece to be locked to the body; and a support for holding the plate and the locking piece spaced by a certain distance and for holding the plate pivotably in a plane of the plate.

This causes the cardiac potential measuring device to have clip structure including the plate, the locking piece, and the support, and the plate holding the electrode units pivots. Accordingly, users can hold the cardiac potential measuring device at a desired position on the body by nipping clothes or the like with the locking piece and the plate, and can measure cardiac potential in arbitrary directions.

These general or specific aspects may be implemented by a system, a method, an integrated circuit, a computer program, or a computer-readable recording medium such as a CD-ROM.

The cardiac potential measuring device, and the cardiac potential measuring method according to exemplary embodiments of the present disclosure will be described below with reference to the drawings.

First Exemplary Embodiment

FIG. 1 is a block diagram illustrating a configuration of a cardiac potential measuring system according to a first exemplary embodiment of the present disclosure. The cardiac potential measuring system is a system for measuring and presenting cardiac potential, and includes cardiac potential measuring device 110a and terminal device 111.

Cardiac potential measuring device 110a illustrated in FIG. 1 is a device configured to measure cardiac potential and to calculate a preferable attachment direction (preferred attachment direction) of an electrode. Cardiac potential measuring device 110a includes first electrode 101, second electrode unit 102, attachment direction detector 103, potential difference acquisition unit 104, accumulator 105, attachment direction calculator 106, and transmitter 107.

Terminal device 111 is a terminal configured to present various information items including cardiac potential measured by cardiac potential measuring device 110a, and includes receiver 108 configured to receive information transmitted from cardiac potential measuring device 110a, and presentation unit 109 configured to present the information received by receiver 108. For example, terminal device 111 is a smart phone, a personal computer (PC), or a receiving terminal dedicated to the present cardiac potential measuring system.

First, each component of cardiac potential measuring device 110*a* will be described.

<First Electrode 101 and Second Electrode Unit 102>

First electrode 101 is a sensor unit including one of a pair of electrodes attached to a user. Second electrode unit 102 is a sensor unit including the other one of the pair of electrodes attached to the user.

For example, first electrode 101 and second electrode unit 102 each include the electrode made of a material such as silver chloride. Each of first electrode 101 and second electrode unit 102 may be an active electrode further having an amplifier circuit and inhibiting noise generated in a lead wire or the like that conveys a signal from the electrode. The active electrode enables measurement of cardiac potential without a paste.

<Potential Difference Acquisition Unit 104>

Potential difference acquisition unit 104 is a processing unit for acquiring a potential difference between first electrode 101 and second electrode unit 102 as cardiac potential. For example, potential difference acquisition unit 104 is a circuit electrically connected to first electrode 101 and second electrode unit 102, the circuit measuring the potential difference (cardiac potential) between first electrode 101 and second electrode unit 102. Potential difference acquisition unit 104 may be a processing unit connected to a measuring circuit for measuring the potential difference between first electrode 101 and second electrode unit 102, the processing unit acquiring the potential difference from the measuring circuit.

When potential of a living body is measured, signal processing such as high-pass filtering or low-pass filtering is commonly applied because a noise or a drift phenomenon occurs. Potential difference acquisition unit 104 performs such signal processing in the present exemplary embodiment. When an electrocardiogram is measured, potential difference acquisition unit 104 may perform processing for extracting peaks from the potential and calculating a heart rate.

In the present exemplary embodiment, cardiac potential measuring device 110*a* includes two electrodes (first electrode 101 and second electrode unit 102). Cardiac potential measuring device 110*a* may include three or more electrode units. A device for measuring living body potential typically includes an electrode unit for acquiring ground potential in order to secure stability of potential. The present exemplary embodiment may also be configured such that one electrode selected from among first electrode 101 and second electrode unit 102 is connected to a ground, the selected one electrode is a place that functions as the ground and a reference point for potential measurement, and a difference between potential at the place described above and potential at the other electrode unit is measured to measure the potential difference between first electrode 101 and second electrode unit 102. In the present exemplary embodiment, the following description assumes that first electrode 101 is the reference point (ground) for measurement.

FIGS. 2A to 2C are external appearance (structure) diagrams of the cardiac potential measuring system according to the present exemplary embodiment. In the present exemplary embodiment, as illustrated in FIG. 2A, potential difference acquisition unit 104 is connected to first electrode 101 and second electrode unit 102 with lead wires. Attachment direction detector 103, potential difference acquisition unit 104, accumulator 105, attachment direction calculator 106 (above components 103 to 106 are implemented by a microcomputer, for example), and transmitter 107 (implemented by, for example, a communication module for Bluetooth (registered trademark)) are mounted on processing substrate 112, and cardiac potential measuring device 110*a* of the present exemplary embodiment is implemented as a circuit module.

FIG. 2B is a diagram illustrating an example of sticking plaster type (patch type) cardiac potential measuring device 110*a* using the circuit module illustrated in FIG. 2A. Cardiac potential measuring device 110*a* is formed on a pad that can be stuck on a body. Cardiac potential measuring device 110*a* can be attached to the body, in a similar way to sticking a plaster on the body. First electrode 101 is disposed in a vicinity of processing substrate 112, and second electrode unit 102 is disposed a predetermined distance away from first electrode 101. This patch type cardiac potential measuring device 110*a* is attached to a predetermined position of the body to measure potential. The measured potential is transmitted to terminal device 111, such as a smart phone as illustrated in FIG. 2C, via communication lines, such as Bluetooth (registered trademark), and is displayed in presentation unit 109 of terminal device 111.

Figure 3:
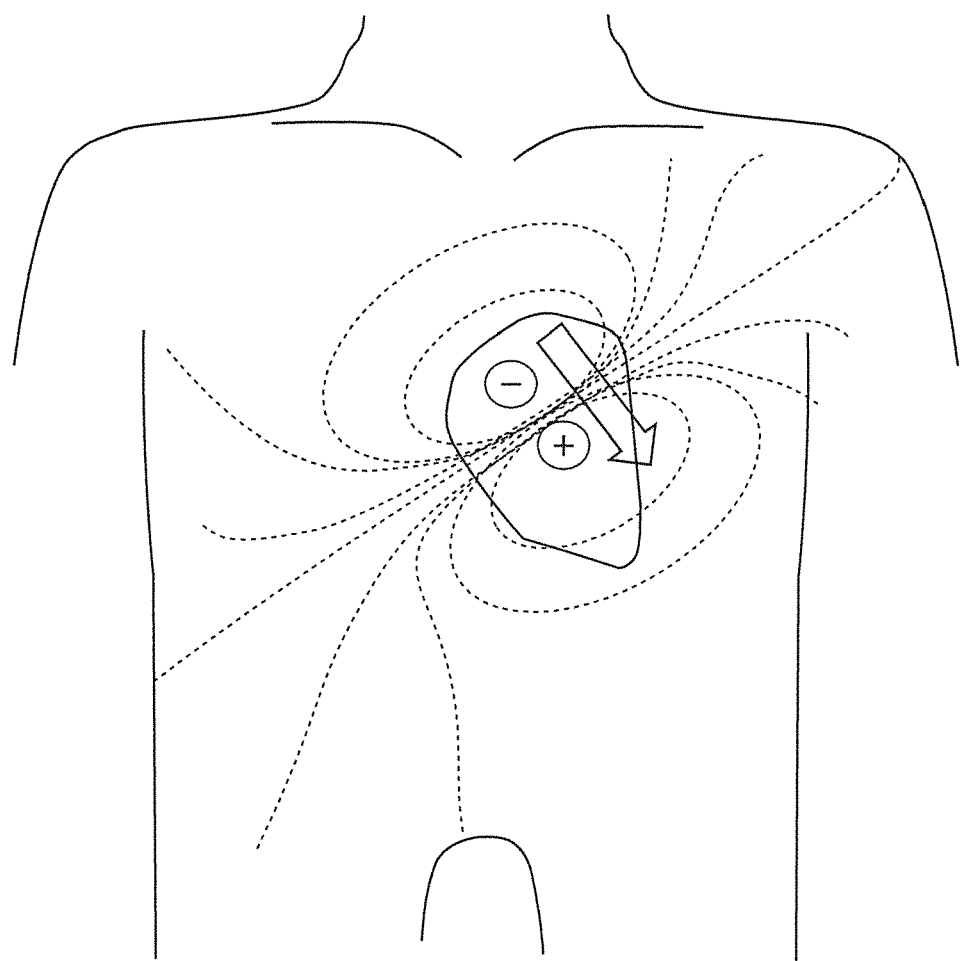
FIG. 3 is a diagram illustrating potential distribution of a human.

FIG. 3 is a diagram illustrating potential distribution generated by activities of a human heart when viewed from front. As illustrated in FIG. 3, the heart is positioned slightly on a left side of a center of a chest in the body, and is positioned tilting sideways with a distal end (apex) down.

The heart performs repeated muscular movement of contraction and relaxation caused by potential change (depolarization and repolarization) in a cell. An electrocardiogram is a diagram showing a result of measurement of the potential distribution generated by this potential change on a body surface, projectively from a predetermined position and angle. The potential distribution is changed by contraction or relaxation of an atrium or a ventricle on a time-series basis, which occurs as a P wave, QRS waves (R wave), and a T wave in the electrocardiogram. In the present exemplary embodiment, the following description focuses on excitation of the ventricle (R wave). This is because the potential elevated by ventricular excitation is highest in cardiac potential, and is an important factor for clinical reasons, such as measurement of a heart rate, and for measuring conditions of health or disease in daily life.

Dotted lines in FIG. 3 illustrate an example of the potential distribution that occurs on the body surface at the time of the R wave. A position and tilt of the heart, and polarization of potential at a time of ventricular excitation cause predetermined potential distribution on the body surface. This potential distribution is dependent on the position and direction of the heart, and components forming the body, such as skin and fat, and thus differs for every user.

Figure 4:
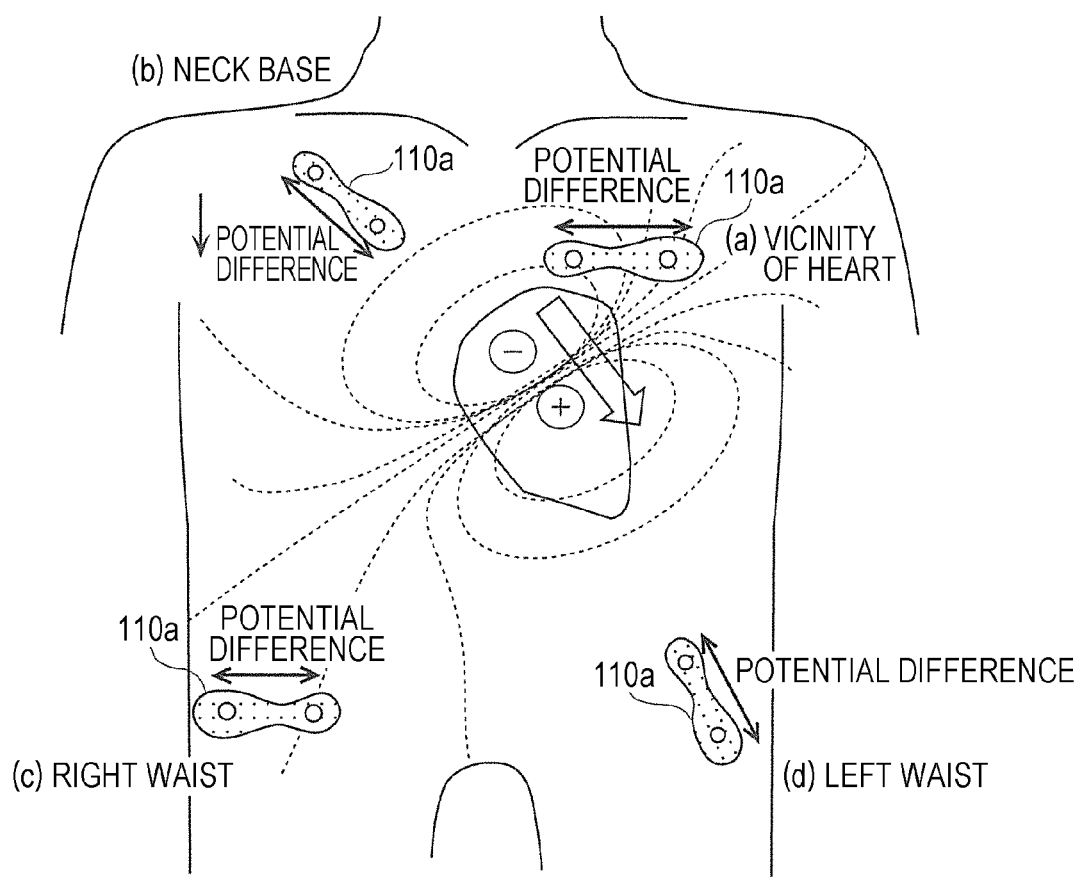
FIG. 4 is a diagram illustrating an attachment state of the cardiac potential measuring device and measured potential differences according to the first exemplary embodiment.

FIG. 4 is a diagram illustrating an attachment state (attachment position and attachment direction) of cardiac potential measuring device 110*a* according to the present exemplary embodiment, and measured potential differences. As an example of attachment of patch type cardiac potential measuring device 110*a* on the body surface, FIG. 4 illustrates an example of attachment at four places (vicinity of the heart ((a) of FIG. 4), neck base ((b) of FIG. 4), right waist ((c) of FIG. 4), and left waist ((d) of FIG. 4)). The potential difference between first electrode 101 and second electrode unit 102 at each attachment position is measured as cardiac potential. As illustrated in FIG. 4, a potential gradient (that is, the potential difference) caused by the potential distribution differs depending on the positions (attachment positions) and directions (attachment directions) in which cardiac potential measuring device 110a is attached. The potential difference becomes larger as the attachment position is closer to the heart, and the potential difference becomes smaller as the attachment position is distant from the heart. Even at a common attachment position, the gradient differs depending on the attachment direction, that is, the potential difference also differs.

The attachment direction or the attachment direction of cardiac potential measuring device 110a refers to a direction of a virtual line that connects first electrode 101 and second electrode unit 102, and in more detail to a direction of a virtual line that connects an electrode included in first electrode 101 and an electrode included in second electrode unit 102. When the virtual line is a straight line, the direction of the line is a direction parallel to the line, and includes positive and negative directions. When the virtual line is a curve, the direction of the line is a tilt of the line at a predetermined position between first electrode 101 and second electrode unit 102, or a direction of a line that indicates the tilt of the line. The direction of the line that indicates the tilt includes positive and negative directions. The virtual line has an identical line shape relative to first electrode 101 (or second electrode unit 102), regardless of the positions of first electrode 101 and second electrode unit 102. In addition to the line that connects a center of the electrode included in first electrode 101 and a center of the electrode included in second electrode unit 102, the virtual line includes a line that connects some position of the electrode included in first electrode 101 and some position of the electrode included in second electrode unit 102. The attachment direction or the attachment direction of cardiac potential measuring device 110a may be just a direction in which first electrode 101 and second electrode unit 102 are aligned.

In particular, if simple measurement is to be made daily, the attachment near the chest may be complicated. Simple attachment of the electrodes to the neck base or the waist enables general users to use the cardiac potential measuring device easily and daily, and enables support for a life free from worry about health. However, since the neck base and waist are distant from the heart, the potential difference may be small, and signals from the electrodes may be buried in a noise.

The present exemplary embodiment describes, particularly even at an attachment position distant from the heart, a technique for calculating the preferred attachment direction of cardiac potential measuring device 110a at such a position, thereby enabling measurement of the cardiac potential that has been impossible, or enabling measurement of more precise cardiac potential.

<Attachment Direction Detector 103>

Attachment direction detector 103 is a processing unit configured to detect the attachment direction (more strictly speaking, the direction of the virtual line that connects first electrode 101 and second electrode unit 102) of cardiac potential measuring device 110a. For example, attachment direction detector 103 includes at least one of an acceleration sensor, a gyroscope, and an altitude sensor.

Figure 5:
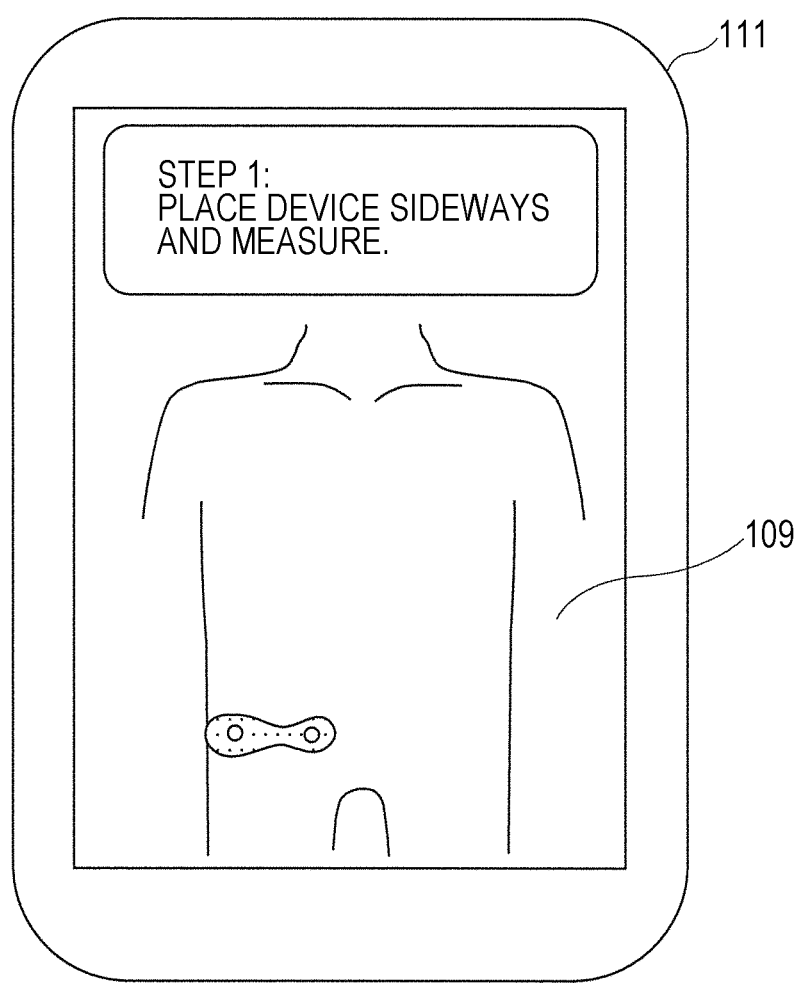
FIG. 5 is a diagram illustrating an example of presentation (an example of presentation urging a first attachment state) made by a terminal device according to the first exemplary embodiment.

FIG. 5 is a diagram illustrating an example of presentation made by terminal device 111 when cardiac potential is measured (an example of presentation urging a first attachment state). In FIG. 5, a message (image) saying "Place the device sideways and measure" is displayed in presentation unit 109 of terminal device 111, such as a smart phone. Here, sideways placement means placement in a horizontal direction. In accordance with this display, the user attaches cardiac potential measuring device 110a to the body in the first attachment state (sideways in the present example) to measure the potential difference. The first attachment state refers to a state where first electrode 101 and second electrode unit 102 are attached to the body side by side in an arbitrary attachment direction. The first attachment state includes a case where cardiac potential measuring device 110a is attached in accordance with the message displayed in presentation unit 109, as illustrated in FIG. 5.

Figure 6:
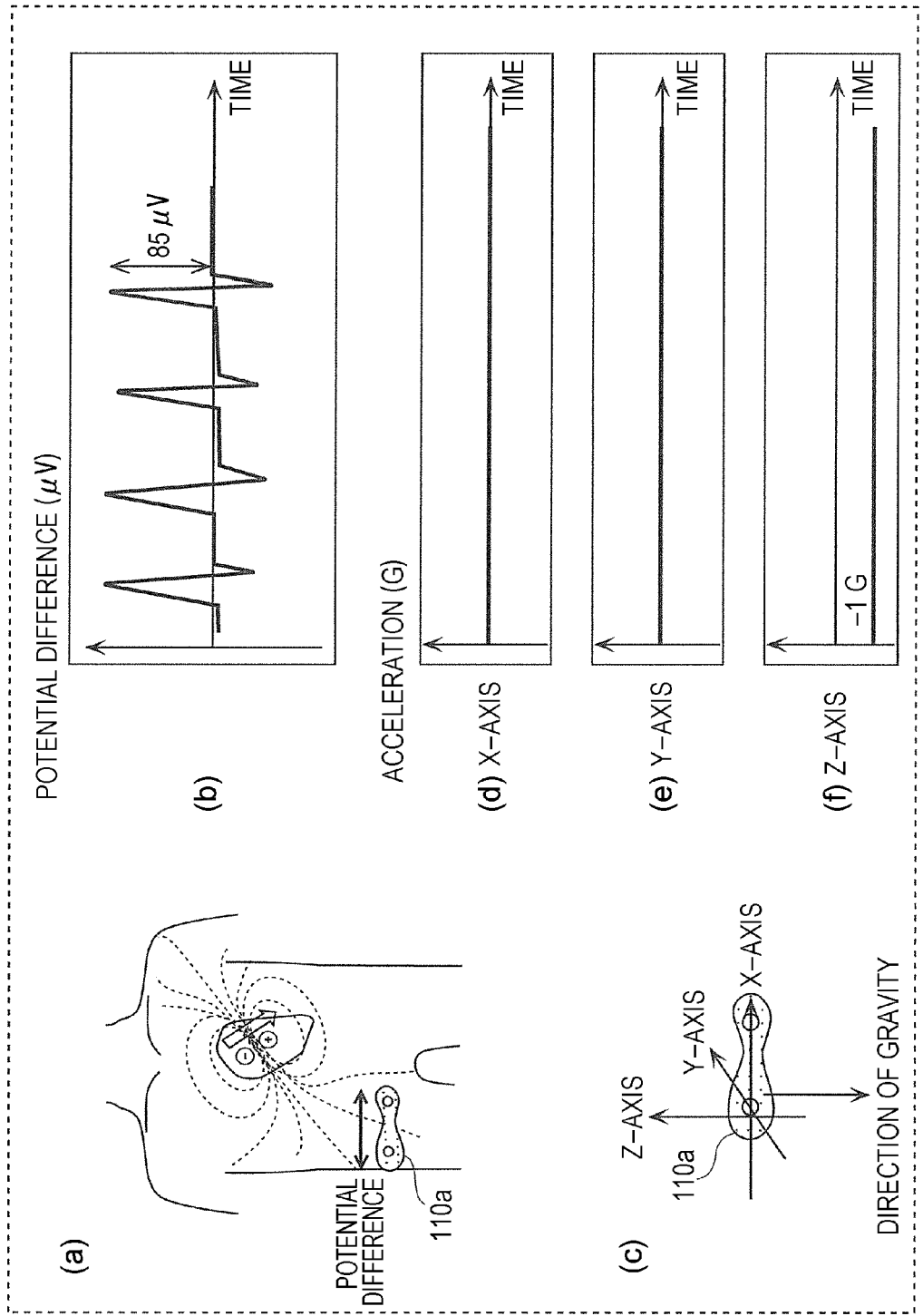
FIG. 6 are diagrams illustrating measurement of a potential difference in the first attachment state.

FIG. 6 are diagrams illustrating measurement of the potential difference in the first attachment state. FIG. 6 illustrate the attachment state (the first attachment state) of cardiac potential measuring device 110a, the potential difference acquired by potential difference acquisition unit 104, a direction of acceleration detected by attachment direction detector 103, detected acceleration in an X-axis, acceleration in a Y-axis, and acceleration in a Z-axis, respectively. As illustrated in (a) of FIG. 6, cardiac potential measuring device 110a is attached sideways (horizontally) to the waist. As the potential difference accompanying activities of the heart, cardiac potential is measured and illustrated as an electrocardiogram ((b) of FIG. 6). As illustrated in (b) of FIG. 6, the potential difference measures 85 µV at the peak of the R wave. As a peak detection method, general techniques, such as a correlational method or a zero-cross method, are known, and these general techniques are used also in the present exemplary embodiment.

Attachment direction detector 103 detects the attachment direction of cardiac potential measuring device 110a in such a first attachment state. Attachment direction detector 103 is an acceleration sensor that detects acceleration of three-axis directions as illustrated in (c) of FIG. 6. As illustrated in (d) to (f) of FIG. 6, as the acceleration sensor, attachment direction detector 103 indicates 0 G in the X-axis direction, 0 G in the Y-axis direction, and −1 G in the Z-axis direction. Based on a result of such acceleration detection and a vertical direction of gravity, cardiac potential measuring device 110a is attached so as to be orthogonal to the gravity direction in the first attachment state, and can detect that cardiac potential is being measured.

Figure 7:
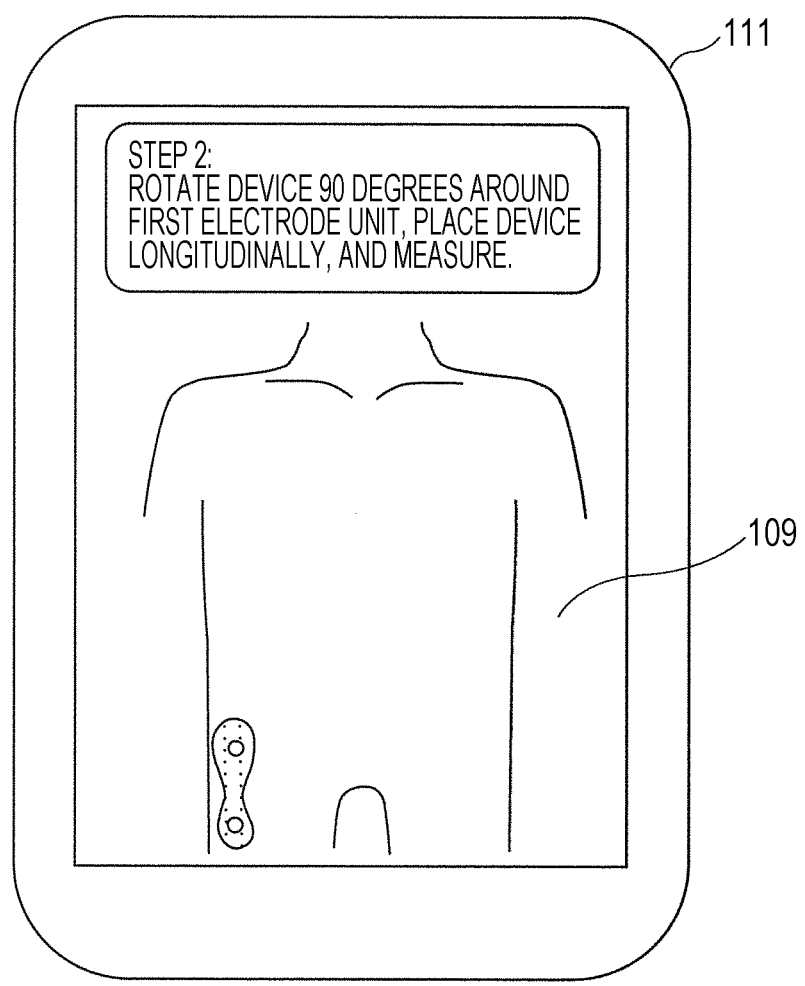
FIG. 7 is a diagram illustrating an example of presentation (an example of presentation urging a second attachment state) made by the terminal device according to the first exemplary embodiment.

FIG. 7 is a diagram illustrating an example of presentation made by terminal device 111 when cardiac potential (an example of presentation urging a second attachment state) is measured. In FIG. 7, a message saying "Rotate the device 90 degrees around the first electrode unit, place the device in a longitudinal direction, and measure." is displayed in presentation unit 109 of terminal device 111, such as a smart phone. Here, the longitudinal direction means a vertical direction. In accordance with this display, the user attaches cardiac potential measuring device 110a to the body in the second attachment state (longitudinal direction in the present example) to measure the potential difference. The second attachment state refers to a state where first electrode 101 and second electrode unit 102 are attached to the body side by side in an arbitrary attachment direction different from the attachment direction of the first attachment state. The second attachment state includes a case where cardiac potential measuring device 110a is attached in accordance with the message displayed in presentation unit 109, as illustrated in FIG. 7.

For example, it is preferable to dispose first electrode 101 and second electrode unit 102 in the second attachment state on a circle and within a predetermined distance from the circle having a radius of a distance from a center between first electrode 101 and second electrode unit 102 to first electrode 101 (second electrode unit 102) in the first attachment state.

Figure 8:
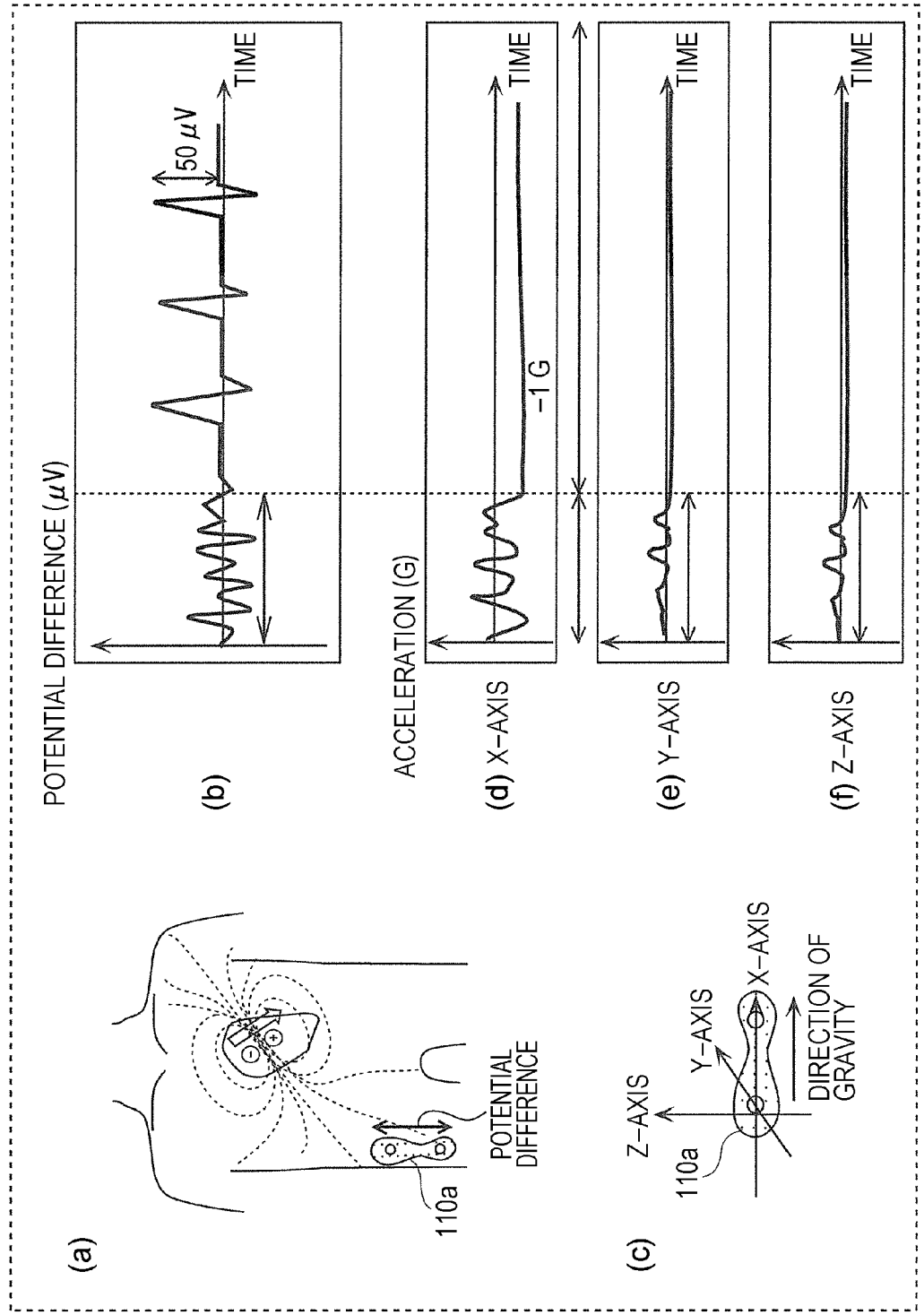
FIG. 8 are diagrams illustrating measurement of the potential difference in the second attachment state.

FIG. 8 are diagrams illustrating measurement of the potential difference in the second attachment state, and (a) to (f) of FIG. 8 correspond to (a) to (f) of FIG. 6 illustrating the measurement result in the first attachment state, respectively. (a) to (f) of FIG. 8 illustrate the potential difference ((b) of FIG. 8) and acceleration ((d) to (f) of FIG. 8) during a period from a time when the message urging measurement in the second attachment direction illustrated in FIG. 7 is presented to a time when the user rotates the attachment direction of cardiac potential measuring device 110a by 90 degrees ((a) of FIG. 8) and measures in the longitudinal direction. As illustrated in (b) of FIG. 8, the potential difference in the longitudinal direction measures 50 μV at the peak of the R wave. Attachment direction detector 103 detects the attachment direction of cardiac potential measuring device 110a in such a second attachment state. In this second attachment state, attachment direction detector 103 functions as an acceleration sensor that detects acceleration of the three-axis directions illustrated in (c) of FIG. 8. As illustrated in (d) to (f) of FIG. 8, in the second attachment state, attachment direction detector 103 indicates, as the acceleration sensor, −1 G in the X-axis direction, 0 G in the Y-axis direction, and 0 G in the Z-axis direction. From such an acceleration detection result, it is detected in the second attachment state that cardiac potential measuring device 110a is attached in a direction identical to the gravity direction, and that the cardiac potential is measured in this state.

<Accumulator 105>

Accumulator 105 is a storage unit configured to associate the attachment direction detected by attachment direction detector 103 with the potential difference acquired by potential difference acquisition unit 104, and to accumulate the attachment direction and the potential difference. FIG. 9 is a diagram illustrating an example of information accumulated in accumulator 105. FIG. 9 illustrates the attachment directions (here, acceleration of the X-axis, Y-axis, and Z-axis directions) and the potential differences in the attachment directions in each of the first attachment state and the second attachment state.

<Attachment Direction Calculator 106>

Attachment direction calculator 106 is a processing unit configured to calculate and output the preferred attachment direction that is the attachment direction in which the potential difference larger than any one of a first potential difference and a second potential difference is generated, based on: (1) the first potential difference that is the potential difference acquired by potential difference acquisition unit 104 in a case where first electrode 101 and second electrode unit 102 are attached to the body of the user in a first attachment state; (2) the second potential difference that is the potential difference acquired by potential difference acquisition unit 104 in a case where first electrode 101 and second electrode unit 102 are attached to the body of the user in a second attachment state; and (3) a first attachment direction that is the attachment direction detected by attachment direction detector 103 in the first attachment state, and a second attachment direction that is the attachment direction detected by attachment direction detector 103 in the second attachment state, or an angle made by the first attachment direction and the second attachment direction. In the present exemplary embodiment, attachment direction calculator 106 calculates, as the preferred attachment direction, a direction in which a maximum potential gradient is generated at the attachment position, from the first attachment direction and the second attachment direction, and the potential differences (the first potential difference and the second potential difference) in the first attachment direction and the second attachment direction, respectively, accumulated in accumulator 105. FIG. 10A is a diagram illustrating an example of calculation of a direction of the maximum potential gradient (preferred attachment direction) made by attachment direction calculator 106.

As illustrated in FIG. 10A, the potential gradient that appears on the body surface can be expressed by a vector with bases of two axes of a plane to measure. It is assumed here that the bases are e1 and e2. Each of the potential differences (vectors) in the first attachment direction and the second attachment direction (for example, assume that the potential difference is acquired in the direction orthogonal to the first attachment direction) is broken down into components of an axis e1 and an axis e2, and components of the axis e1 and the axis e2 after synthesis are an x1 and an x2, respectively. In the present exemplary embodiment, when it is assumed that the axis e1 is orthogonal to the gravity direction and the axis e2 is parallel with the gravity direction (that is, identical to the gravity direction) for simplifying the description, a vector (x1, x2), which is a vector sum of two potential differences obtained in the first attachment direction and the second attachment direction, becomes the direction of the maximum potential gradient. The potential difference in the direction can be expressed by Equation 1 below.

[Equation 1]

$$|\nabla \varphi| = \sqrt{\left(\frac{\partial \varphi}{\partial e_1}\right)^2 + \left(\frac{\partial \varphi}{\partial e_2}\right)^2} = \sqrt{x_1^2 + x_2^2} \quad \text{(Equation 1)}$$

Accordingly, in the present example, the direction of the maximum potential gradient will be a direction (85, 50) with the bases e1 and e2, that is, when a clockwise angle relative to the base e1 is θ, tan θ=50/85, and the direction of the maximum potential gradient will be a direction of an angle of about 30 degrees.

In this way, attachment direction calculator 106 calculates the direction in which the maximum potential gradient is generated from the vector specified by the first potential difference and the first attachment direction and the vector specified by the second potential difference and the second attachment direction, and calculates the direction as the preferred attachment direction. That is, attachment direction calculator 106 calculates the direction in which the maximum potential gradient is generated as the preferred attachment direction, based on the first potential difference and the first attachment direction in the first attachment state, and on the second potential difference and the second attachment direction in the second attachment state. Instead of the first attachment direction and the second attachment direction, an angle that is made by the first attachment direction and the second attachment direction may be used. This is because, if the angle made by the two vectors is known, the maximum potential gradient (relative to one of the two vectors) is knows from the two vectors.

Figure 10B:
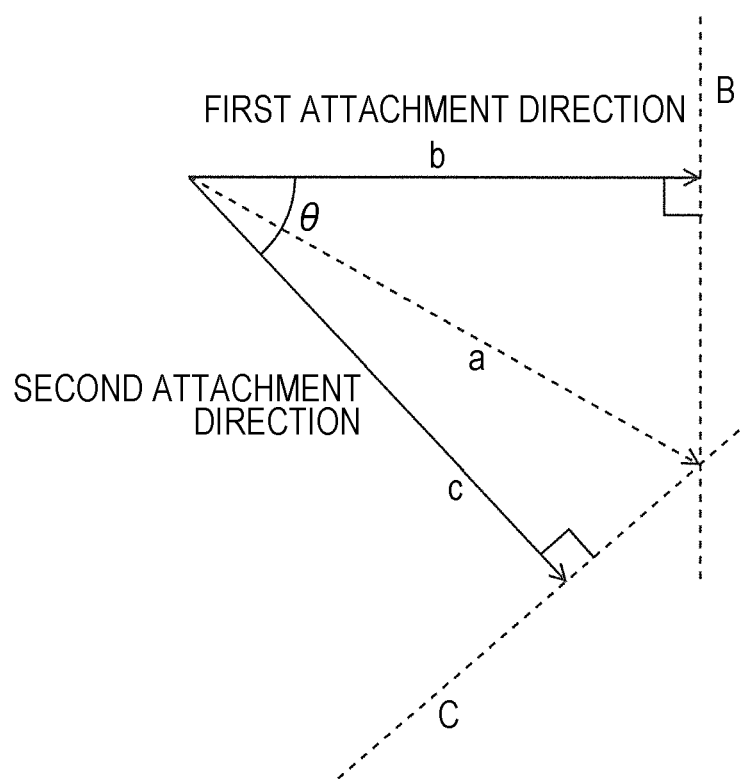
FIG. 10B is a diagram illustrating another example of calculation of the preferred attachment direction according to the first exemplary embodiment.

An example of calculation of the preferred attachment direction in a case where the first attachment direction and the second attachment direction are not orthogonal to each other will be described with reference to FIG. 10B. FIG. 10B is a diagram illustrating the example of calculation of the direction of the maximum potential gradient (preferred attachment direction) by attachment direction calculator 106 in a case where the first attachment direction and the second attachment direction are not orthogonal to each other. It is assumed that a vector a is the maximum potential gradient at the position, and that a vector b is detected as the first attachment direction, and that |b| is detected as the first potential difference. Since the first potential difference |b| is detected as a vector b component (a component in the direction of the vector b) of the vector a, the vector a (that is, a distal end of the vector a) will exist on a perpendicular line to the vector b, that is, on the straight line B. Next, it is assumed that the attachment direction is rotated by an angle θ, and that a vector c is detected as the second attachment state, and that |c| is detected as the second potential difference. Similarly, the vector a (that is, the distal end of the vector a) will exist on the straight line C. Accordingly, the maximum potential gradient can be calculated through solution of Equation 2 below about the vector a.

[Equation 2]

$$\cos^{-1}\left(\frac{b}{a}\right) + \cos^{-1}\left(\frac{c}{a}\right) = \theta \quad \text{(Equation 2)}$$

That is, vector a=(|b|−(cos θ/tan θ) (|b|−|c|cos θ)+|c|sin θ), which is the maximum potential gradient, will be obtained by using b that serves as one reference, the other reference c, and θ. In this way, attachment direction calculator 106 calculates the direction in which the maximum potential gradient is generated from the vector specified by the first potential difference and the first attachment direction, and from the vector specified by the second potential difference and the second attachment direction. Attachment direction calculator 106 then calculates the direction in which the maximum potential gradient is generated as the preferred attachment direction.

Although the attachment direction of cardiac potential measuring device 110a is horizontal and vertical in order to provide easier-to-understand description in the present exemplary embodiment, the attachment direction is not limited to these examples. As long as the two bases of the first attachment direction and the second attachment direction are not parallel to each other, it is theoretically possible to calculate the maximum potential gradient. However, since an influence of a noise or an error is large under actual environments, it is preferable to measure with the angle made by the two attachment directions close to 90 degrees within a 90-degree limit.

<Transmitter 107>

Transmitter 107 is a communication interface configured to transmit the preferred attachment direction (information indicating the preferred attachment direction) calculated by attachment direction calculator 106 to terminal device 111 by communications. For example, transmitter 107 transmits the information indicating the preferred attachment direction to terminal device 111 wirelessly in accordance with the Bluetooth (registered trademark) standard.

Note that, among the components included in cardiac potential measuring device 110a illustrated in FIG. 1, accumulator 105 and transmitter 107 are not essential components as the cardiac potential measuring device according to the present disclosure. Even without accumulator 105, attachment direction calculator 106 can calculate the preferred attachment direction by receiving the first attachment direction and the second attachment direction directly from attachment direction detector 103, and by receiving the first potential difference and the second potential difference directly from potential difference acquisition unit 104. Even without transmitter 107, attachment direction calculator 106 can present the preferred attachment direction to the user by outputting the calculated preferred attachment direction to another processing unit, such as a voice output unit.

Next, each component of terminal device 111 will be described.

<Receiver 108>

Receiver 108 is a communication interface configured to receive the preferred attachment direction transmitted from cardiac potential measuring device 110a and to output the preferred attachment direction to presentation unit 109. For example, receiver 108 receives the information indicating the preferred attachment direction transmitted wirelessly from terminal device 111 in accordance with the Bluetooth (registered trademark) standard, and outputs the information to presentation unit 109.

<Presentation Unit 109>

Figure 11:
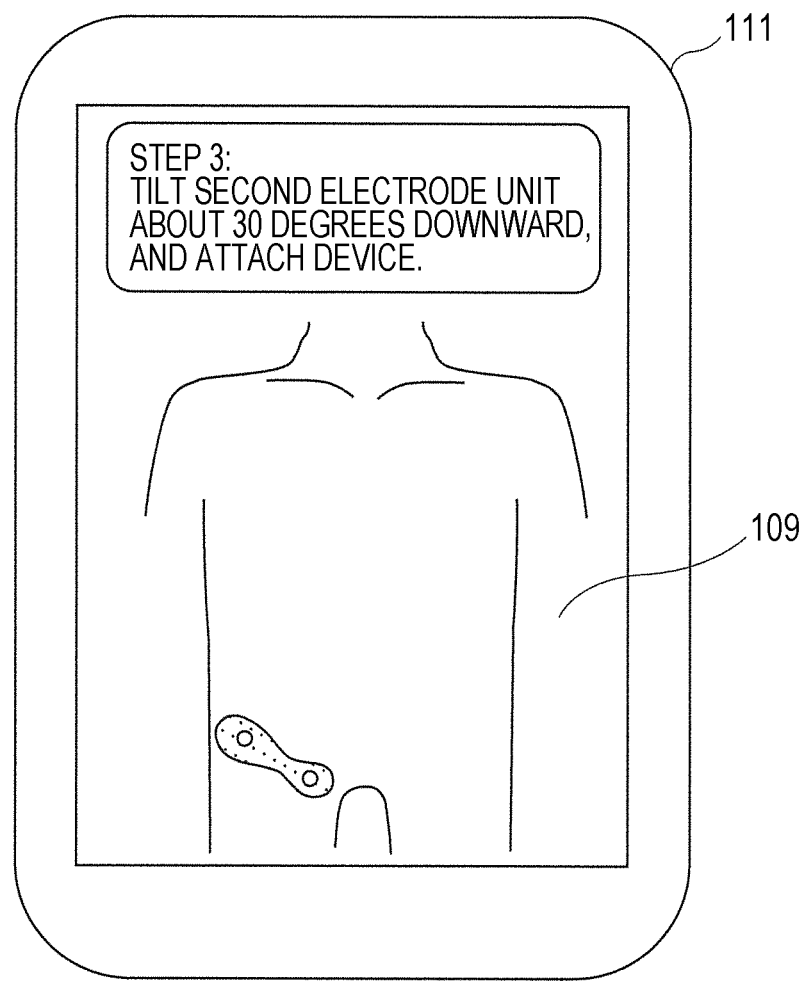
FIG. 11 is a diagram illustrating an example of presentation of the preferred attachment direction according to the first exemplary embodiment.

Presentation unit 109 is a processing unit configured to present the user various information items such as the preferred attachment direction received from cardiac potential measuring device 110a through receiver 108, that is, various information items including the preferred attachment direction calculated by attachment direction calculator 106. For example, presentation unit 109 is a display such as an LCD, a loudspeaker, a processor that executes a program, and the like. FIG. 11 is a diagram illustrating an example of presentation of the preferred attachment direction made by presentation unit 109. Here, a message saying "Lower the second electrode unit by about 30 degrees, and attach the measuring device" is displayed on a screen (presentation unit 109) of terminal device 111, such as a smart phone. presentation unit is expressed with display unit.

Next, an operation (cardiac potential measuring method) of the cardiac potential measuring system configured as described above according to the present exemplary embodiment will be described.

Figure 12:
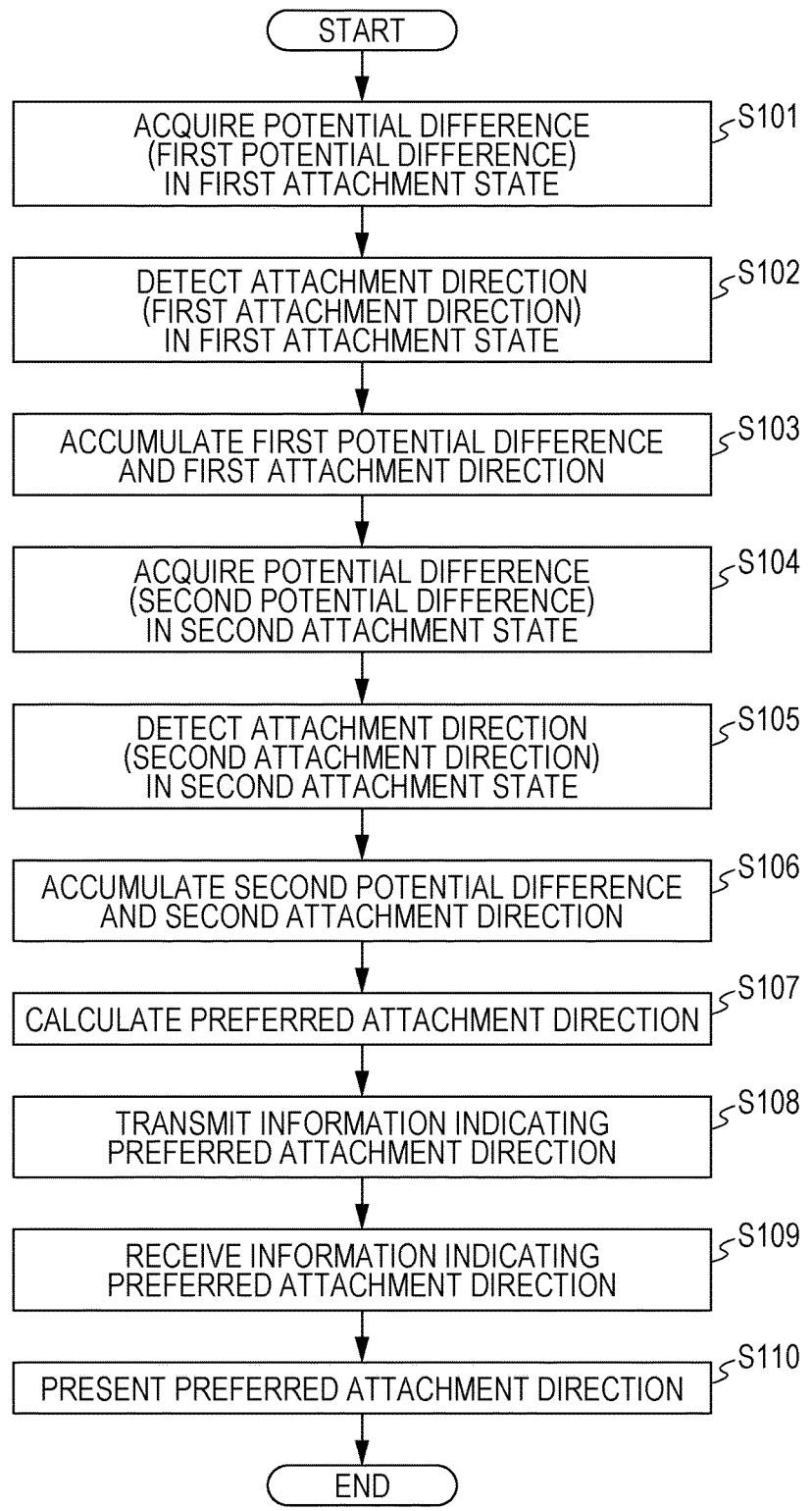
FIG. 12 is a flow chart illustrating an operation of the cardiac potential measuring system according to the first exemplary embodiment.

FIG. 12 is a flow chart illustrating the operation of the cardiac potential measuring system according to the first exemplary embodiment. Steps S101 to S108 are executed by cardiac potential measuring device 110a, whereas steps S109 to S110 are executed by terminal device 111.

First, potential difference acquisition unit 104 acquires the potential difference between first electrode 101 and second electrode unit 102 when first electrode 101 and second electrode unit 102 are attached to the user in the first attachment state, that is, the first potential difference, as the cardiac potential (S101). This step S101 corresponds to a first step of acquiring, by potential difference acquisition unit 104, the first potential difference that is the potential difference between first electrode 101 and second electrode unit 102 as the cardiac potential in a case where first electrode 101 and second electrode unit 102 are attached to the body in the first attachment state.

Subsequently, attachment direction detector 103 detects the attachment direction (first attachment direction) of cardiac potential measuring device 110a in the first attachment state, that is, the direction of the virtual line that connects first electrode 101 and second electrode unit 102 (S102).

Then, the first potential difference acquired in step S101 and the first attachment direction detected in step S102 are accumulated in accumulator 105 by potential difference acquisition unit 104 and attachment direction detector 103, respectively (S103).

In this stage, as illustrated in FIG. 6, for example, the potential difference when cardiac potential measuring device 110a is attached sideways in the waist measures 85 μV at the peak of the R wave.

Next, measurement in the second attachment state is performed. That is, as in the first attachment state, potential difference acquisition unit 104 acquires the potential difference (cardiac potential) between first electrode 101 and second electrode unit 102 in the second attachment state as the second potential difference (S104). Subsequently, attachment direction detector 103 detects the attachment direction of cardiac potential measuring device 110a in the second attachment state, that is, the second attachment direction (S105). Furthermore, the second potential difference and the second attachment direction are accumulated in accumulator 105 (S106). The above step S104 corresponds to a second step of acquiring, by potential difference acquisition unit 104, the second potential difference that is the potential difference between first electrode 101 and second electrode unit 102 as the cardiac potential in a case where first electrode 101 and second electrode unit 102 are attached to the body in the second attachment state.

In this stage, as illustrated in FIG. 8, for example, the potential difference when cardiac potential measuring device 110a is attached in the longitudinal direction in the waist measures 50 µV at the peak of the R wave.

The procedure that combines the above-described step S102 and step S105 corresponds to a third step of detecting (1) the first attachment direction that is the attachment direction detected by attachment direction detector 103 in the first attachment state, and the second attachment direction that is the attachment direction detected by attachment direction detector 103 in the second attachment state, or (2) the angle made by the first attachment direction and the second attachment direction (the above (1) in the present exemplary embodiment).

Next, by using the first attachment direction, the second attachment direction, the first potential difference, and the second potential difference, attachment direction calculator 106 calculates the preferable attachment direction, in other words, the preferred attachment direction that is the attachment direction in which a potential difference larger than any one of the first potential difference and the second potential difference is generated (S107). This step S107 corresponds to a fourth step of calculating and outputting the preferred attachment direction based on the first potential difference acquired in the above first step, the second potential difference acquired in the second step, and the first attachment direction and the second attachment direction detected in the third step, or the angle made by the first attachment direction and the second attachment direction.

Acquisition of the potential difference by potential difference acquisition unit 104, and detection of the attachment direction by attachment direction detector 103 in the above first attachment state and the second attachment state may be executed in opposite order, and may be executed simultaneously.

Figure 13:
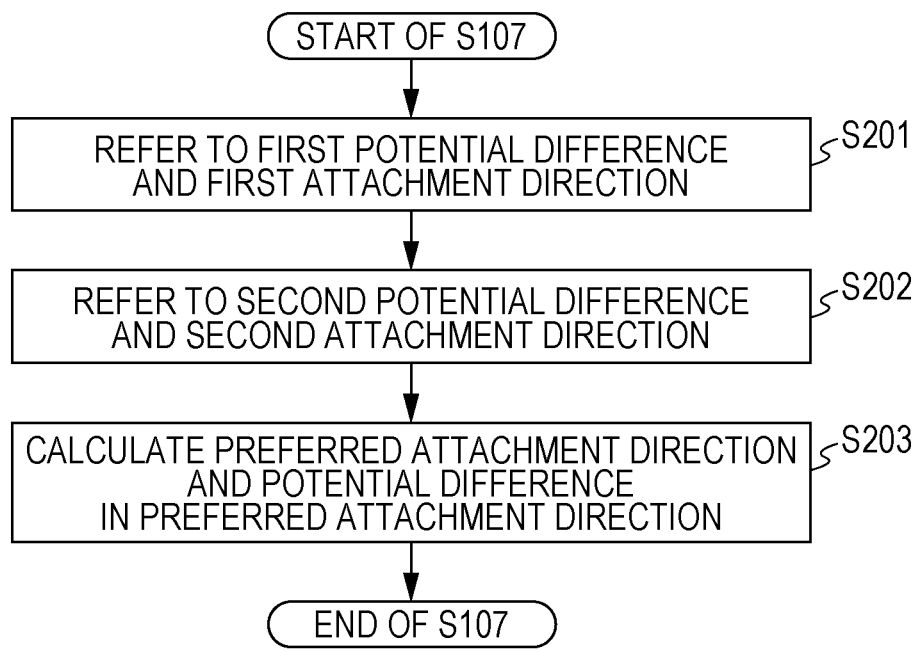
FIG. 13 is a flow chart illustrating a detailed procedure of step S107 (calculation of the preferred attachment direction) in FIG. 12.

FIG. 13 is a flow chart illustrating a detailed procedure of step S107 (calculation of the preferred attachment direction) in FIG. 12. Attachment direction calculator 106 refers to the first attachment direction and the first potential difference accumulated in accumulator 105 (S201), and subsequently refers to the second attachment direction and the second potential difference (S202). The term "refer to" means "read" from accumulator 105.

Attachment direction calculator 106 performs a vector operation from respective attachment directions and potential differences, and calculates the direction of the maximum potential gradient, that is, the preferred attachment direction and the potential difference obtained when measured in the preferred attachment direction (S203). In the case of the present exemplary embodiment, the first and second potential differences are 85 µV when the attachment direction is orthogonal (FIG. 6) to the gravity direction, and 50 µV when the attachment direction is parallel (FIG. 8) to the gravity direction, respectively. Therefore, the direction of the maximum potential gradient (that is, the preferred attachment direction) is calculated to be about 30 degrees with respect to the direction orthogonal to the gravity direction (FIG. 10A).

The obtained preferred attachment direction (information indicating the preferred attachment direction) is transmitted from transmitter 107 (S108), received by receiver 108 (S109), and presented to the user by presentation unit 109 (S110). As a result, as illustrated in FIG. 11, the preferred attachment direction is presented by presentation unit 109 of terminal device 111, such as a smart phone.

This allows the user to know the preferred attachment direction presented by presentation unit 109.

In recent years, small devices capable of simply measuring living body information, including an electrocardiogram, have been developed. This enables measurement of cardiac potential in daily life. It is preferable to attach the cardiac potential measuring device near the heart to measure cardiac potential. However, in order to simply attach the device daily with few restraints, for example, attachment at a position that is not necessarily a vicinity of the heart, such as the neck base or waist that is slightly distant from the heart, may be appropriate. However, distance from the heart inhibits generation of the potential difference and precise measurement. Even at such a distant position, cardiac potential measuring device 110a according to the present exemplary embodiment enables calculation of an appropriate attachment direction suitable for the position, and makes it possible to perform simpler daily measurement and to provide a reassuring and safe life. That is, even general users who are not specialists in cardiac potential measurement can also know more preferable attachment direction by attaching the first electrode and the second electrode unit in the two attachment states for measurement, which enables the general users to measure cardiac potential simply while leading daily life.

Second Exemplary Embodiment

Next, a second exemplary embodiment of the present disclosure will be described.

In the above-described first exemplary embodiment, information on a preferable attachment direction (preferred attachment direction) has been provided. In the present exemplary embodiment, determination is further made about whether a cardiac potential measuring device is attached in the preferable attachment direction (preferred attachment direction).

Figure 14:
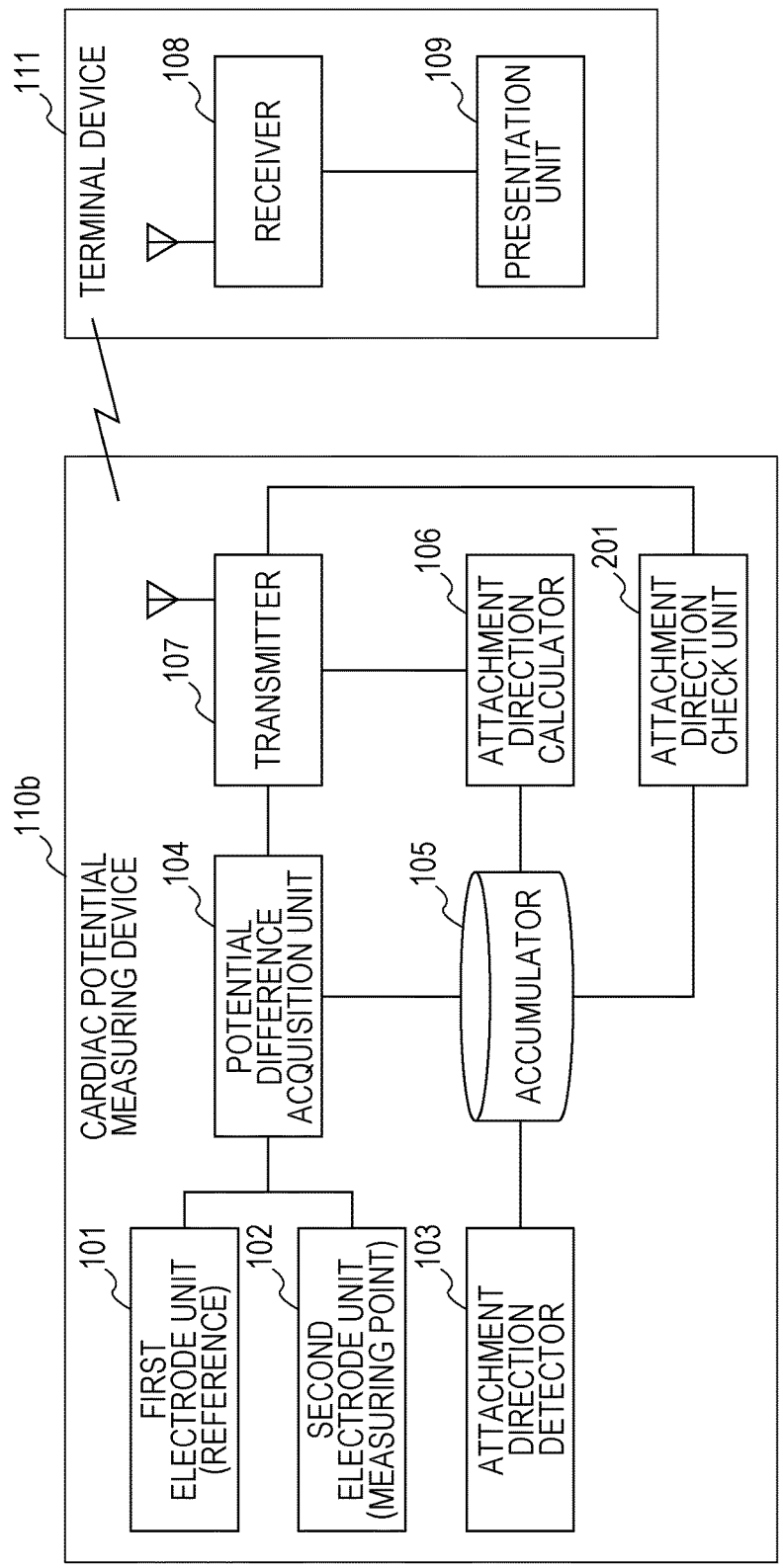
FIG. 14 is a block diagram illustrating a configuration of the cardiac potential measuring system according to a second exemplary embodiment.

FIG. 14 is a block diagram illustrating a configuration of a cardiac potential measuring system according to the second exemplary embodiment of the present disclosure. This cardiac potential measuring system is a system for measuring and presenting cardiac potential, and includes cardiac potential measuring device 110b and terminal device 111. In addition to components of cardiac potential measuring device 110a (FIG. 1) in the first exemplary embodiment, cardiac potential measuring device 110b according to the present exemplary embodiment includes attachment direction check unit 201. Hereinafter, components identical to the components in the first exemplary embodiment have identical reference numerals with no further description, and the description will focus on different points.

Attachment direction check unit 201 is a processing unit configured to compare a potential difference acquired by potential difference acquisition unit 104 with a potential difference in the preferred attachment direction calculated by attachment direction calculator 106, and to present, via presentation unit 109, a message (image) urging reattachment in the preferred attachment direction based on a comparison result.

In the present exemplary embodiment, in addition to calculation of the preferred attachment direction, attachment direction calculator 106 also calculates the potential difference in the preferred attachment direction.

Figures 15, 16:
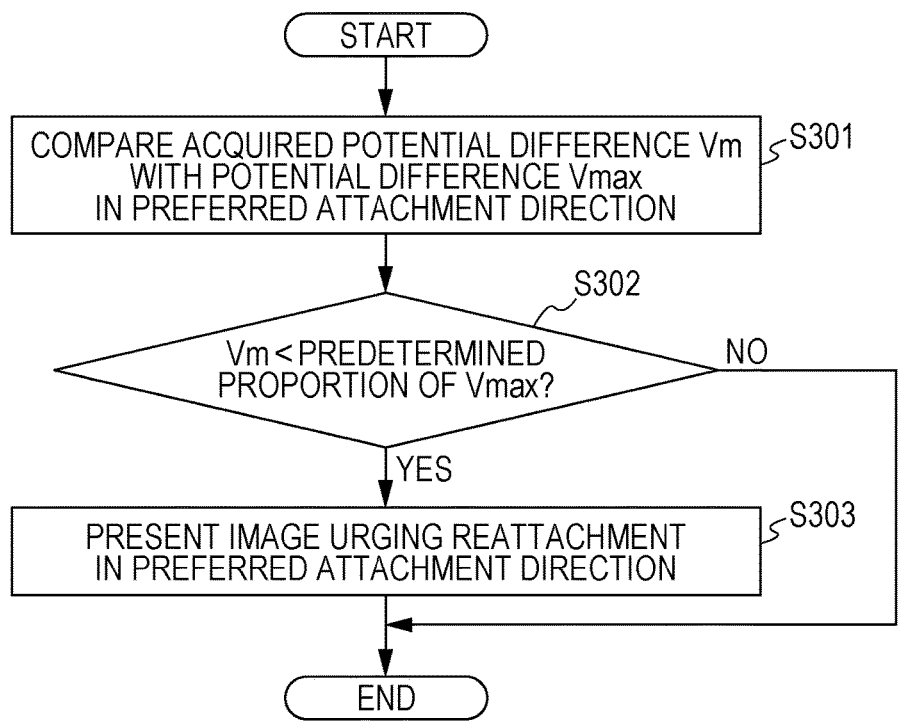
FIG. 15 is a flow chart illustrating an operation of an attachment direction check unit according to the second exemplary embodiment.
FIG. 16 is a diagram illustrating an example of information accumulated in the accumulator according to the second exemplary embodiment.

FIG. 15 is a flow chart illustrating an operation of attachment direction check unit 201 included in cardiac potential measuring device 110*c* according to the present exemplary embodiment.

Attachment direction check unit 201 compares a potential difference Vm acquired by potential difference acquisition unit 104 with a potential difference (potential difference of a maximum potential gradient) Vmax in the preferred attachment direction, the potential difference being already calculated by attachment direction calculator 106 (S301). In a case where the acquired potential difference Vm is less than a predetermined proportion of the potential difference Vmax in the preferred attachment direction (Yes in S302), attachment direction check unit 201 presents the image urging reattachment in the preferred attachment direction via presentation unit 109 (S303). Specifically, attachment direction check unit 201 calculates a difference (angle) between the preferred attachment direction calculated by attachment direction calculator 106 and an actual attachment direction, and presents the message (image) urging a user to modify the attachment direction by the difference (angle) via presentation unit 109. In a case where the acquired potential difference Vm is not less than the predetermined proportion of the potential difference Vmax in the preferred attachment direction (No in S302), attachment direction check unit 201 recognizes that the current attachment state is a correct, appropriate attachment state, and does not present the message (image).

Specific operation of attachment direction calculator 106 will be described below with reference to the drawings.

It is assumed here that attachment direction calculator 106 has also calculated the potential difference in the preferred attachment direction already, in addition to calculation of a direction in which the maximum potential gradient is generated as the preferred attachment direction, based on (1) a first potential difference, (2) a second potential difference, and (3) a first attachment direction and a second attachment direction, or an angle made by the first attachment direction and the second attachment direction. That is, it is assumed that attachment direction calculator 106 has calculated the preferred attachment direction and the potential difference in the preferred attachment direction (potential difference of the maximum potential gradient), based on the first attachment direction and the first potential difference, and on the second attachment direction and the second potential difference. For example, as illustrated in FIG. 10A, it is assumed here that the preferred attachment direction is (85, 50), and that the potential difference in the preferred attachment direction is 100 μV. Attachment direction calculator 106 accumulates these pieces of information in accumulator 105. FIG. 16 is a diagram illustrating an example of the information accumulated in accumulator 105. Information that indicates the preferred attachment direction (85, 50) and the potential difference 100 μV in the preferred attachment direction are accumulated here.

Figure 17:
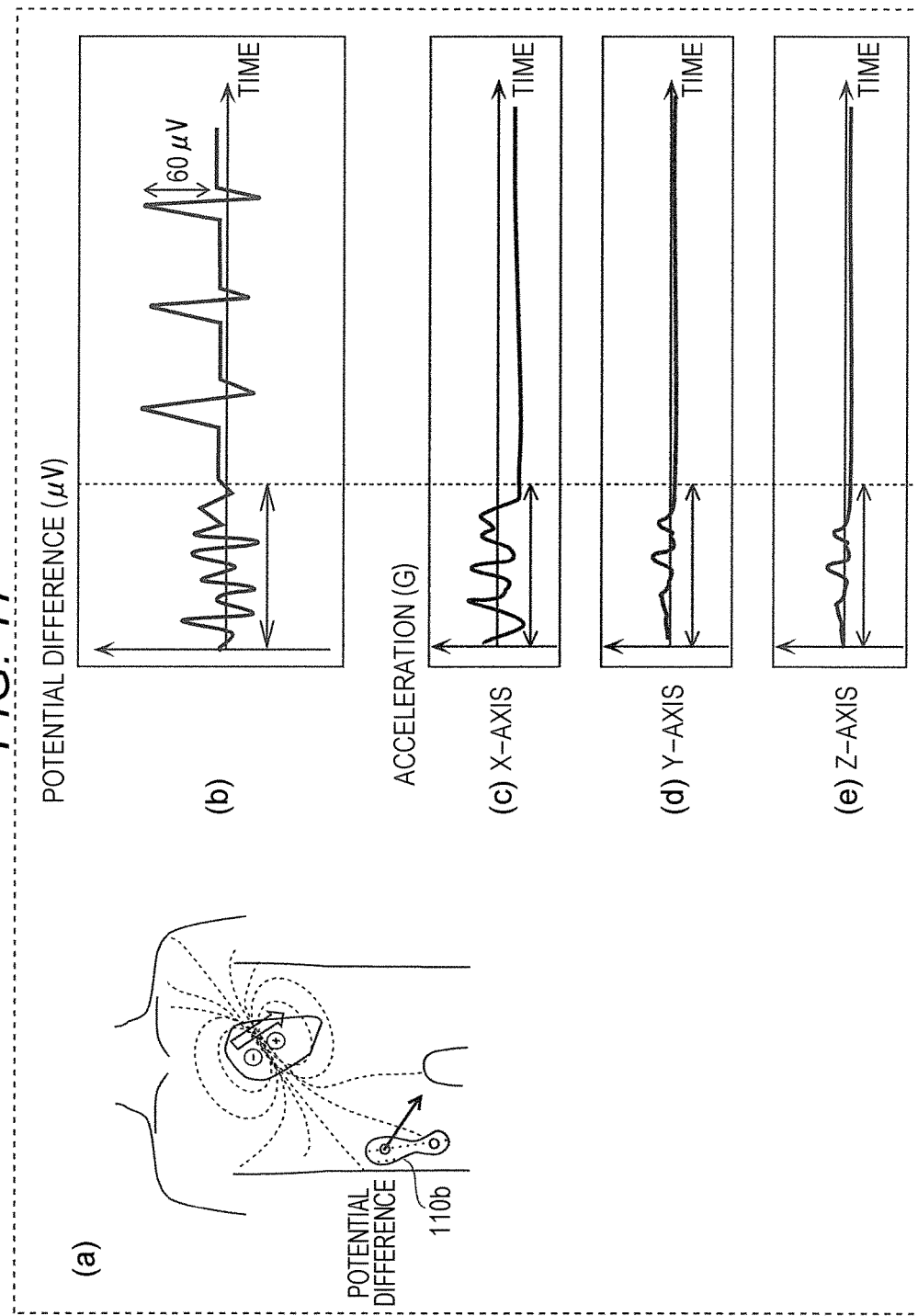
FIG. 17 are diagrams illustrating variations of the potential difference and acceleration with time during a period from a time when the preferred attachment direction is presented to a time when the cardiac potential measuring device is rotated and attached.

FIG. 17 are diagrams illustrating variations of the potential difference acquired by potential difference acquisition unit 104 with time, and variations of acceleration detected by attachment direction detector 103 with time, during a period from a time when the preferred attachment direction (a direction tilted 30 degrees in the present example) is presented via presentation unit 109 as illustrated in FIG. 11 to a time when the user rotates 30 degrees and attaches cardiac potential measuring device 110*b*. FIG. 17 illustrate the attachment state of cardiac potential measuring device 110*b*, the potential difference acquired by potential difference acquisition unit 104, acceleration in an X-axis, acceleration in a Y-axis, and acceleration in a Z-axis detected by attachment direction detector 103, respectively.

After cardiac potential measuring device 110*b* is rotated ((a) of FIG. 17) and attached in a certain attachment direction ((c) to (e) of FIG. 17), the potential difference at a peak of an R wave of cardiac potential measures 60 μV ((b) of FIG. 17). With reference to the information accumulated in accumulator 105, attachment direction check unit 201 compares the potential difference (potential difference in the preferred attachment direction) Vmax to be obtained if cardiac potential measuring device 110*b* is attached in the preferred attachment direction, with the actually acquired potential difference Vm, and calculates a ratio (or a difference) of Vmax to Vm. Based on this ratio, for example, in a case where the potential difference Vm is less than a predetermined proportion of the potential difference Vmax, attachment direction check unit 201 determines that the attachment direction of cardiac potential measuring device 110*b* has deviated, and presents this deviation of the attachment direction to the user via communication and presentation unit 109. For example, in a case where the acquired potential difference Vm is less than 80% of the potential difference Vmax in the preferred attachment direction, this comparison result is presented to the user. In the present example, measurement in a 30-degree tilted position provides the potential difference of only 60 μV while the potential difference of 100 μV is supposed to be provided, and the acquired potential difference is less than 80 μV (=100 μV×0.8). Therefore, attachment direction check unit 201 presents this comparison result (the result indicating that the acquired potential difference is less than the predetermined proportion of the potential difference in the preferred attachment direction) to the user via presentation unit 109.

Figure 18:
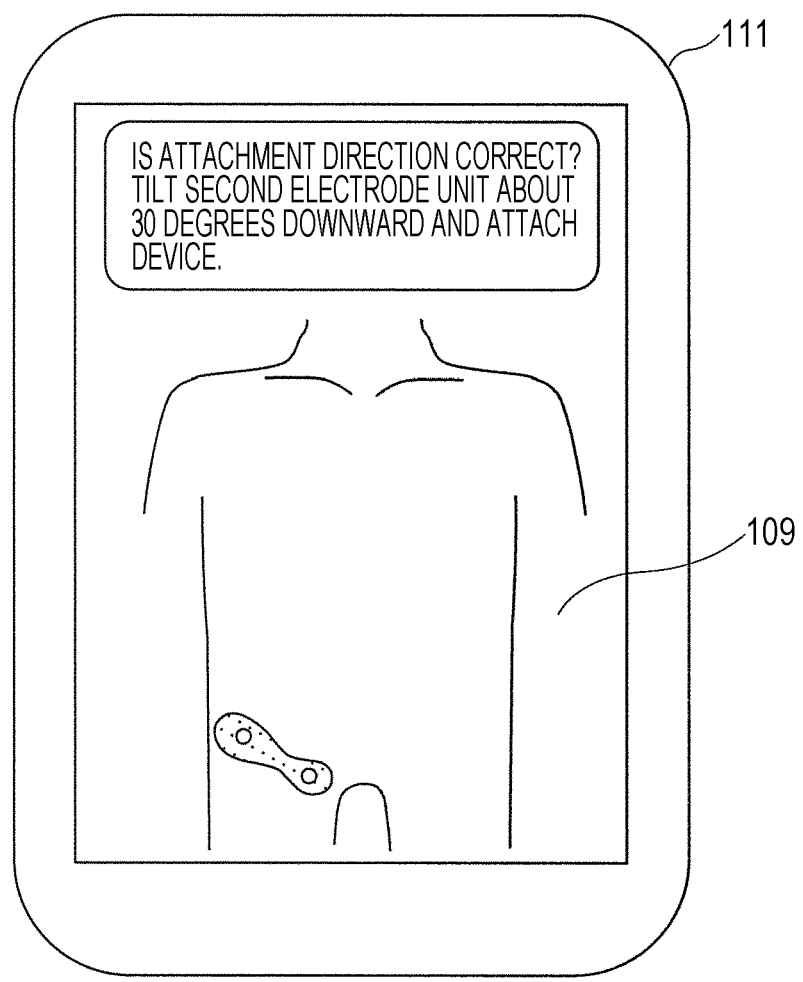
FIG. 18 is a diagram illustrating an example of presentation made by the attachment direction check unit according to the second exemplary embodiment.

FIG. 18 is a diagram illustrating an example of presentation made by attachment direction check unit 201 in a case where the acquired potential difference is less than the predetermined proportion of the potential difference in the preferred attachment direction. In FIG. 18, presentation unit 109 of terminal device 111, such as a smart phone, displays a message saying "Is the attachment direction correct? Tilt the second electrode unit about 30 degrees downward and attach the measuring device."

A potential gradient of an R wave that is largest in cardiac potential is typically tilted from right side to left side from a characteristic of the body, and a direction of the potential gradient also differs from user to user. Moreover, the potential gradient that occurs on the body surface also varies by various factors, and is not uniform. Therefore, it is difficult in some cases to calculate the direction of the potential gradient at a predetermined position, and to further attach cardiac potential measuring device 110*b* in a direction different for every user and every position. As described in the present exemplary embodiment, it becomes possible to measure cardiac potential more simply and properly, by indicating a difference in the attachment direction (deviation angle) based on the calculated preferred attachment direction, the potential difference in the calculated preferred attachment direction, and the actual potential difference.

Figure 19:
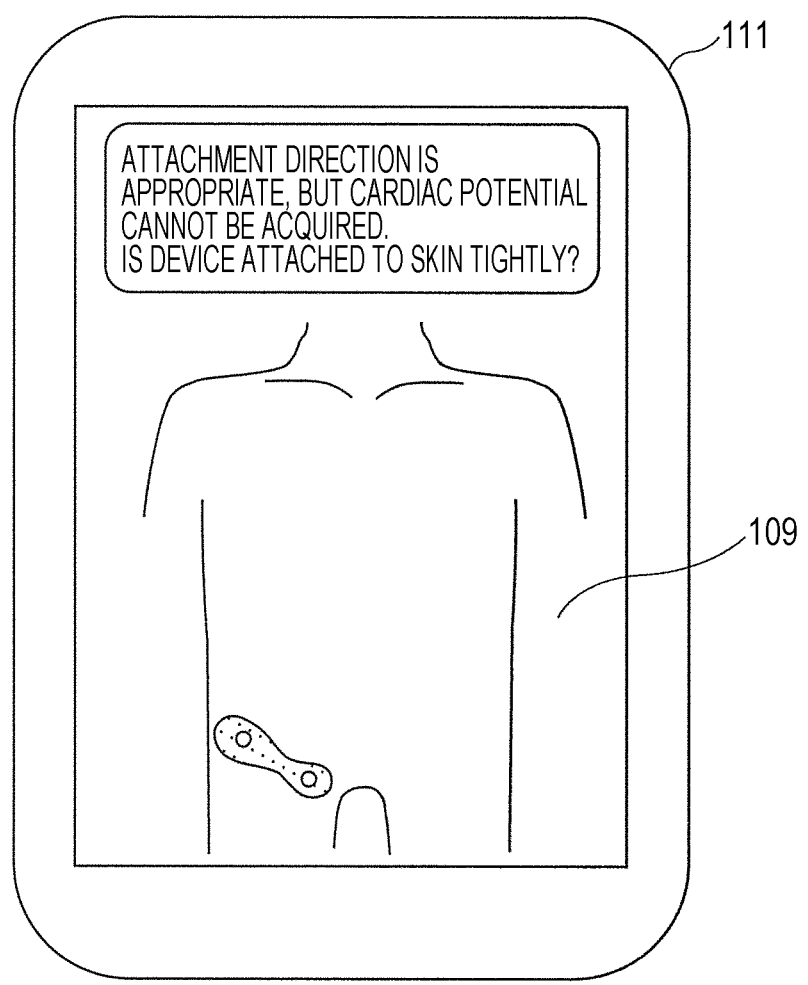
FIG. 19 is a diagram illustrating another example of presentation made by the attachment direction check unit according to the second exemplary embodiment.

In the present exemplary embodiment, cardiac potential measuring device 110b includes attachment direction detector 103, and may determine whether the actual attachment direction is close to the preferred attachment direction by using information obtained by attachment direction detector 103. For example, as illustrated in FIG. 17, attachment direction detector 103 detects acceleration and angular velocity during a period from a time when the preferred attachment direction is indicated to a time when cardiac potential measuring device 110b is attached, and integrates the detected acceleration and angular velocity, so that a distance and rotation can be calculated, and the attachment direction when cardiac potential measuring device 110b is actually attached can be calculated. For example, attachment direction detector 103 detects acceleration and angular velocity of cardiac potential measuring device 110b during a period from the second attachment state to a time when cardiac potential measuring device 110b is attached again in the preferred attachment direction, and accumulator 105 accumulates information, so that the attachment direction in another attachment can be calculated from the accumulated information. At this time, even if another attachment direction is correct (even if the direction coincides with the preferred attachment direction), the potential difference may not be obtained depending on attachment conditions of the electrodes (first electrode 101 and second electrode unit 102). Therefore, even if the attachment direction in another attachment is close to the preferred attachment direction (for example, a direction having an angle less than 10 degrees clockwise or counterclockwise relative to the preferred attachment direction), in a case where the acquired potential difference is less than the predetermined proportion (for example, 80%) of the potential difference that is supposed to be obtained in the preferred attachment direction, information regarding attachment conditions may be presented. FIG. 19 is a diagram illustrating an example of presentation in such a case (a case where the acquired potential difference is less than the predetermined proportion of the potential difference in the preferred attachment direction although the attachment direction is close to the preferred attachment direction). Presentation unit 109 of terminal device 111, such as a smart phone, displays a message saying "The attachment direction is appropriate, but cardiac potential cannot be acquired. Is the device attached to skin tightly?", and presents that there is a problem in the attachment conditions.

As described above, according to the present exemplary embodiment, in a case where there is a large difference between the measured potential difference and the potential difference in the known preferred attachment direction, reattachment in the preferred attachment direction is urged via presentation unit 109, which avoids low-precision cardiac potential measurement due to inadequate attachment direction.

That is, in a case of the small cardiac potential measuring device for simple daily measurement as described in the present exemplary embodiment, unlike electrocardiographs used by health care professionals such as doctors at a hospital, electrodes are not necessarily attached securely. In addition, active electrodes may be used without paste, and cardiac potential obtained may differ significantly depending on the attachment conditions of the electrodes. As described in the present exemplary embodiment, the preferred attachment direction and the potential difference in the preferred attachment directions are calculated, and information regarding the attachment condition is presented to the user based on comparison of the actually acquired potential difference with the potential difference in the preferred attachment direction. This allows the user to attach cardiac potential measuring device 110b more accurately, and to measure cardiac potential simply and properly.

Third Exemplary Embodiment

Next, a third exemplary embodiment of the present disclosure will be described.

The present exemplary embodiment determines whether an attachment position of a cardiac potential measuring device in a second attachment state is appropriate with respect to an attachment position of the cardiac potential measuring device in a first attachment state in the above-described first or second exemplary embodiment.

Figure 20:
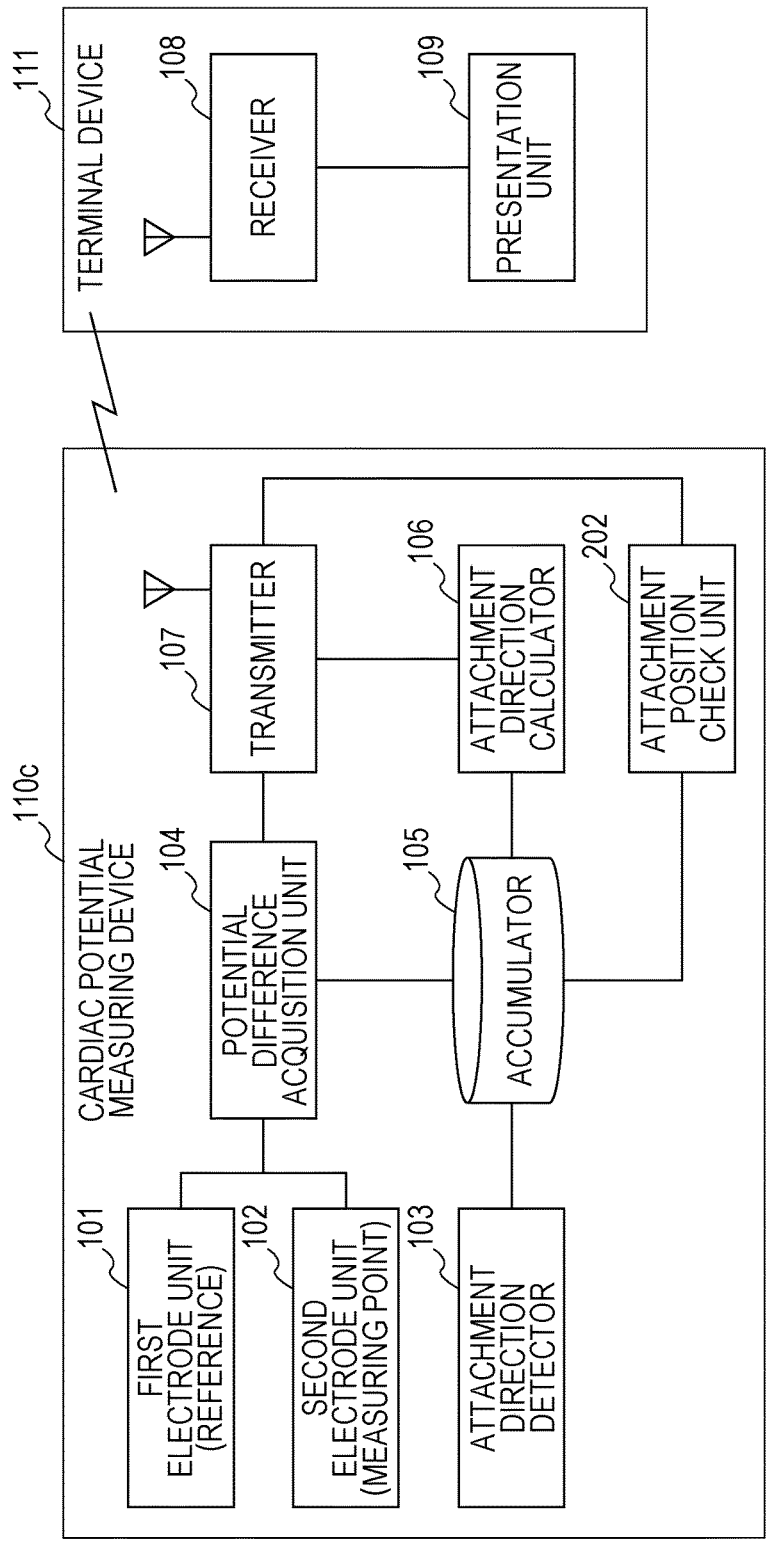
FIG. 20 is a block diagram illustrating a configuration of the cardiac potential measuring system according to a third exemplary embodiment.

FIG. 20 is a block diagram illustrating a configuration of a cardiac potential measuring system according to the third exemplary embodiment of the present disclosure. This cardiac potential measuring system is a system configured to measure and present cardiac potential, and includes cardiac potential measuring device 110c and terminal device 111. In addition to components of cardiac potential measuring device 110a (FIG. 1) in the first exemplary embodiment, cardiac potential measuring device 110c includes attachment position check unit 202. Hereinafter, components identical to the components in the first exemplary embodiment have identical reference numerals with no further description, and the description will focus on different points.

Attachment position check unit 202 is a processing unit configured to determine whether the position of first electrode 101 in the first attachment state and the position of first electrode 101 in the second attachment state are within a predetermined range. For example, attachment position check unit 202 determines whether a distance from a circumference having a radius of a distance from a center between first electrode 101 and second electrode unit 102 to first electrode 101 (second electrode unit 102) in the first attachment state, to a position of each of first electrode 101 and second electrode unit 102 in the second attachment state is within the predetermined range.

Figure 21:
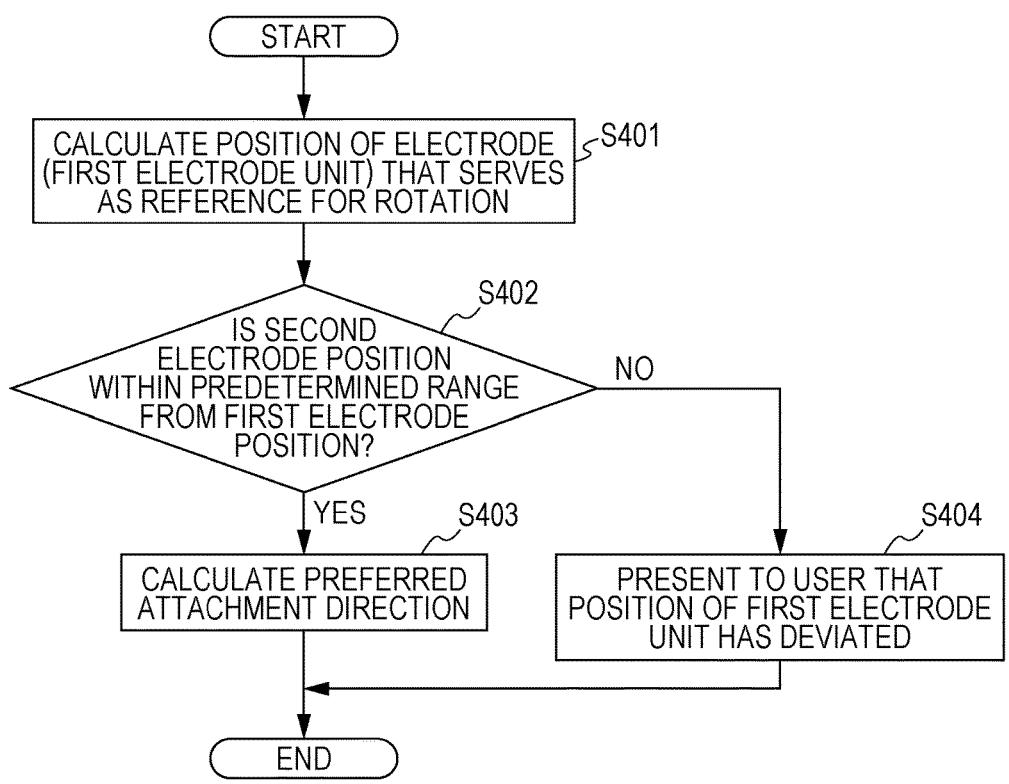
FIG. 21 is a flow chart illustrating an operation of an attachment position check unit according to the third exemplary embodiment.

FIG. 21 is a flow chart illustrating an operation of attachment position check unit 202 included in cardiac potential measuring device 110c according to the present exemplary embodiment. In the present exemplary embodiment, in order to enable determination by attachment position check unit 202, attachment direction detector 103 detects acceleration and angular velocity of cardiac potential measuring device 110c, during a period from a time when the second attachment state is presented to a time when cardiac potential measuring device 110c is attached (in other words, from the first attachment state to the second attachment state), and accumulator 105 accumulates the acceleration and angular velocity.

First, attachment position check unit 202 calculates a trajectory of rotation and movement by integrating the acceleration and angular velocity accumulated in accumulator 105, and calculates a position of an electrode (first electrode 101 in the present example) that serves as reference (center) for rotation (S401). Then, attachment position check unit 202 determines whether a position (a second electrode position) of first electrode 101 in the second attachment state is within the predetermined range with respect to an electrode position (a first electrode position) in the first attachment state (S402). When attachment position check unit 202 determines that the second electrode position is within the predetermined range (for example, within 2 cm around) (Yes in S402), attachment position check unit 202 notifies this determination to attachment direction calculator 106, and in response to the notification, attachment direction calculator 106 calculates a preferred attachment direction (S403). That is, when attachment position check unit 202 determines that the position of the first electrode in the first attachment state and the position of the first electrode unit in the second attachment state are within the predetermined range, attachment direction calculator 106 calculates and outputs the preferred attachment direction. On the other hand, when attachment position check unit 202 determines that the second electrode position is outside the predetermined range with respect to the first electrode position (No in S402), attachment position check unit 202 presents to the user that the second electrode position is outside the predetermined range with respect to the first electrode position, that is, that the position of first electrode 101 has deviated via presentation unit 109, and urges measurement again (S404).

Figure 22:
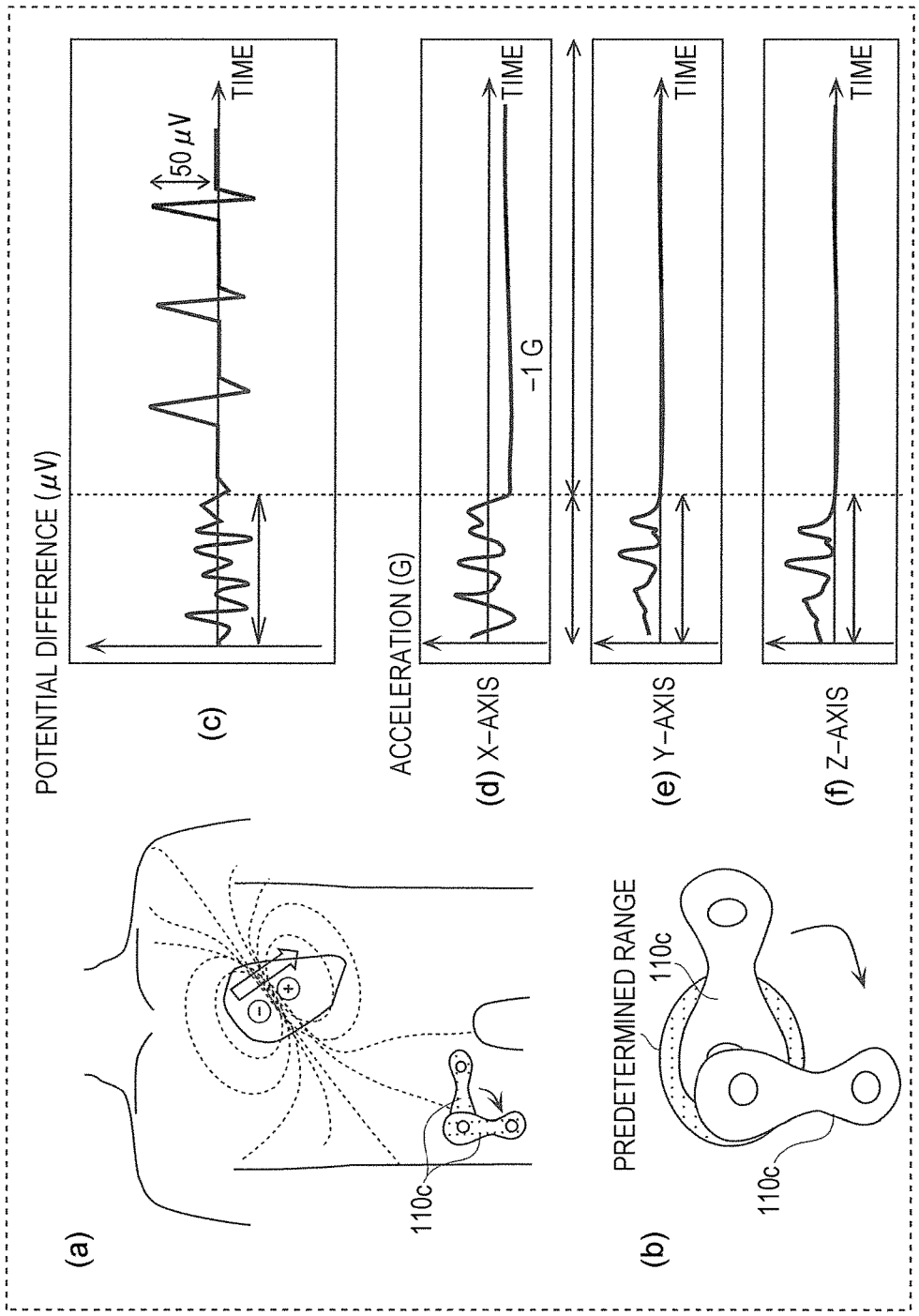
FIG. 22 are diagrams illustrating specific processing performed by the attachment position check unit according to the third exemplary embodiment.

FIG. 22 are diagrams illustrating specific processing performed by attachment position check unit 202 included in cardiac potential measuring device 110c according to the present exemplary embodiment. FIG. 22 illustrate the attachment states (the first attachment state and the second attachment state) of cardiac potential measuring device 110c, a relationship between the first attachment state and the second attachment state, the potential difference acquired by potential difference acquisition unit 104, acceleration in an X-axis, acceleration in a Y-axis, and acceleration in a Z-axis detected by attachment direction detector 103, respectively.

Attachment direction detector 103 detects the acceleration and angular velocity ((a) to (f) of FIG. 22) during a period from a time when the second attachment state is presented to a time when cardiac potential measuring device 110c is attached at a new attachment position ((a) to (b) of FIG. 22), and accumulator 105 accumulates the acceleration and angular velocity. That is, after measurement (acquisition of the potential difference, detection of the attachment direction) in the first attachment state is finished and the second attachment state is presented, the user is going to rotate cardiac potential measuring device 110c and measure in the second attachment state ((a) to (b) of FIG. 22), and data during this period ((c) to (f) of FIG. 22) is accumulated. Attachment position check unit 202 calculates the trajectory of rotation and movement by integrating the accumulated acceleration and angular velocity ((d) to (f) of FIG. 22), and calculates the position of the electrode (first electrode 101 in the present example) that serves as reference for rotation. In the example illustrated in FIG. 22, since first electrode 101 in the second attachment state is positioned within the predetermined range (not deviated here) with respect to the electrode position (the first electrode position) in the first attachment state, as described above, attachment position check unit 202 notifies this information to attachment direction calculator 106, and attachment direction calculator 106 calculates the preferred attachment direction.

Figure 23:
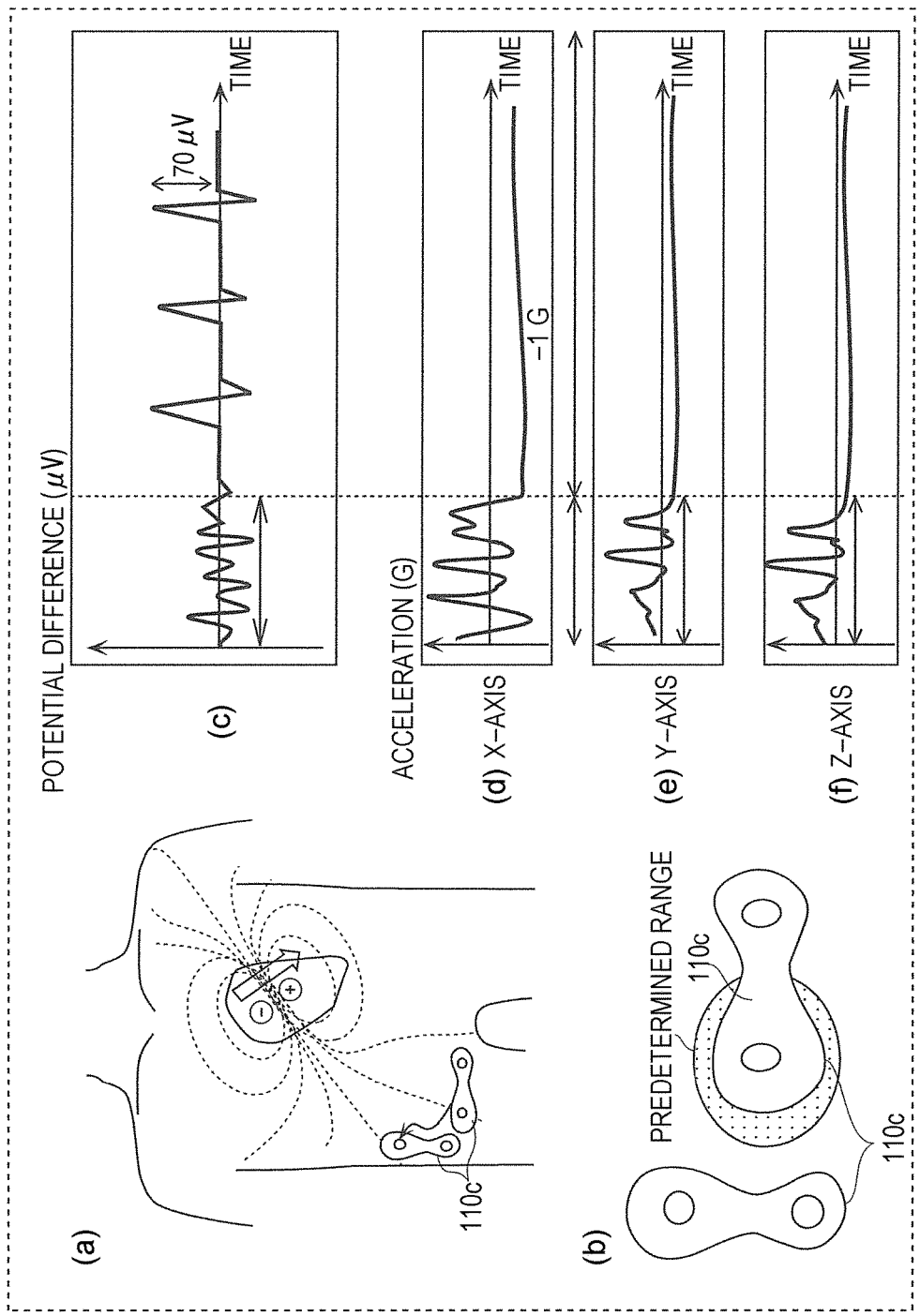
FIG. 23 are diagrams illustrating an example in which a position of a first electrode in the first attachment state and a position in the second attachment state are outside a predetermined range.
Figure 24:
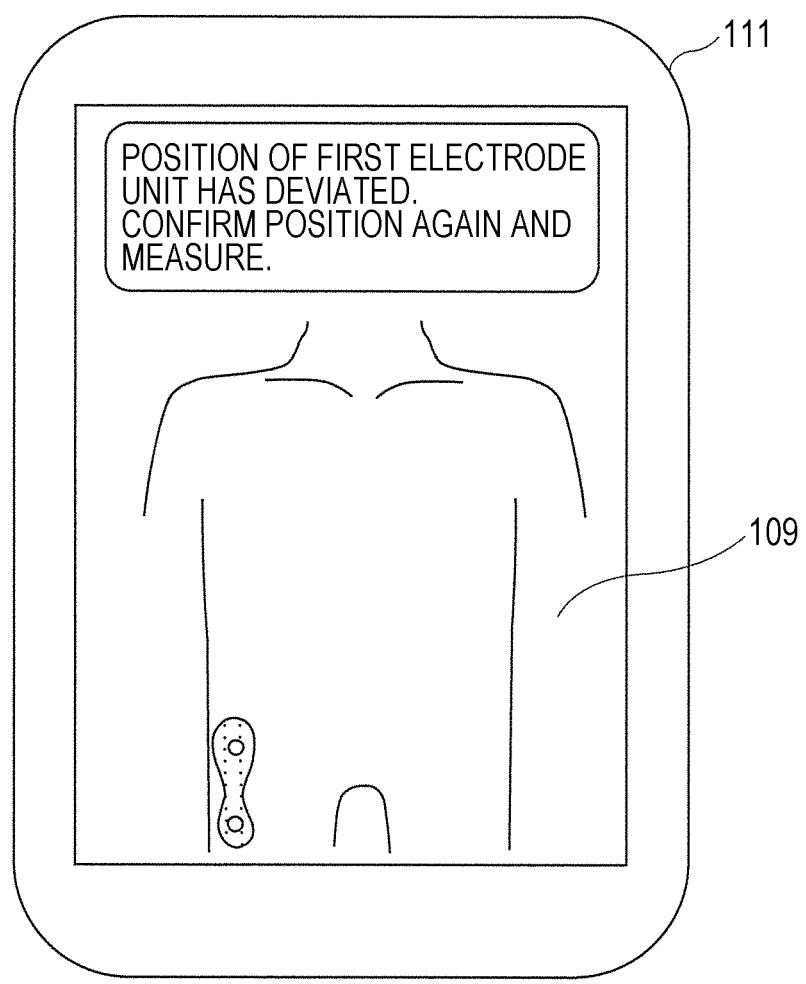
FIG. 24 is a diagram illustrating an example of presentation in a case where a first electrode position is significantly deviated from a second electrode position.

FIG. 23 are diagrams illustrating an example in which the position of first electrode 101 in the first attachment state and the position of first electrode 101 in the second attachment state are outside the predetermined range. FIG. 23 correspond to FIG. 22, respectively. In the example illustrated in FIG. 23, it is calculated from the trajectory of movement and rotation that the position (the second electrode position) of first electrode 101 in the second attachment state is significantly deviated from the position (the first electrode position) of first electrode 101 in the first attachment state. Therefore, attachment position check unit 202 presents this information on deviation to the user via communication (transmitter 107 and receiver 108) and presentation unit 109. FIG. 24 is a diagram illustrating an example of presentation in such a case (a case where the first electrode position is significantly deviated from the second electrode position). Presentation unit 109 of terminal device 111, such as a smart phone, displays a message saying "The position of the first electrode has deviated. Confirm the position again and measure."

As described above, according to the present exemplary embodiment, the preferred attachment direction is calculated only when the position of first electrode 101 that serves as a reference electrode is not significantly deviated between the first attachment state and the second attachment state. This can avoid the problem that the low-precision preferred attachment direction is calculated and presented.

A potential gradient differs depending on a position on a body, as illustrated in FIG. 3 and other drawings. Accordingly, when the attachment position of the electrode is deviated significantly, the gradient is also changed and cannot be calculated accurately. Meanwhile, the cardiac potential measuring device according to the present disclosure, which requires a plurality of measurements, does not necessarily allow measurement at a common reference point in some cases. For example, in a case of a patch type cardiac potential measuring device, when the device is changed from the first attachment state to the second attachment state, that is, when the cardiac potential measuring device needs to be temporarily removed from the body, the position (the attachment position of first electrode unit 101) that serves as reference may be deviated. Although the potential gradient differs depending on the position on the body, if a difference is as small as a predetermined error, the potential gradient is almost identical to the maximum potential gradient, and can be calculated. Therefore, as described above, it is preferable to provide the predetermined range, and to control calculation of the preferred attachment direction depending on whether the attachment position of first electrode 101 is within the predetermined range between the first attachment state and the second attachment state, based on the calculated rotation and trajectory.

When sensors including an acceleration sensor and a gyroscope are used, an initial position of each of the sensors is set as a starting point, and a relative position and relative angle from the starting point will be calculated. Meanwhile, an amount of positional deviation in the present exemplary embodiment needs to be calculated in a rotating system relative to one electrode (first electrode 101). Accordingly, in the present exemplary embodiment, first electrode 101 is preferably provided in a vicinity of the position at which the acceleration sensor (attachment direction detector 103) is mounted on a substrate. This makes estimation of amounts of movement and rotation of first electrode 101 more accurate. However, methods for measuring the amounts of movement and rotation of first electrode 101 are not limited to this method. First electrode 101 and the acceleration sensor (attachment direction detector 103) are installed at relatively distant positions in some cases. In this case, if the acceleration sensor and the gyroscope are used, and if the initial position of each of these sensors are set as the starting point and the relative position and relative angle from the starting point are calculated, the accurate amounts of movement and rotation cannot be calculated because first electrode 101 itself is provided at a position deviated from these sensors. Therefore, for example, a positional relationship between first electrode 101 and the acceleration sensor (attachment direction detector 103) may be previously accumulated, and after taking this positional relationship into consideration, determination may be made whether the position of first electrode unit 101 has deviated.

In the cardiac potential measuring system according to the first to third exemplary embodiments described above, transmitter 107 and receiver 108 are provided, and the preferred attachment direction or the like are presented via presentation unit 109 of terminal device 111 through communications between terminal device 111 for presentation and cardiac potential measuring devices 110a to 110c. However, the configuration is not limited to these examples. Presentation unit 109 may be provided in the cardiac potential measuring device.

Figure 25:
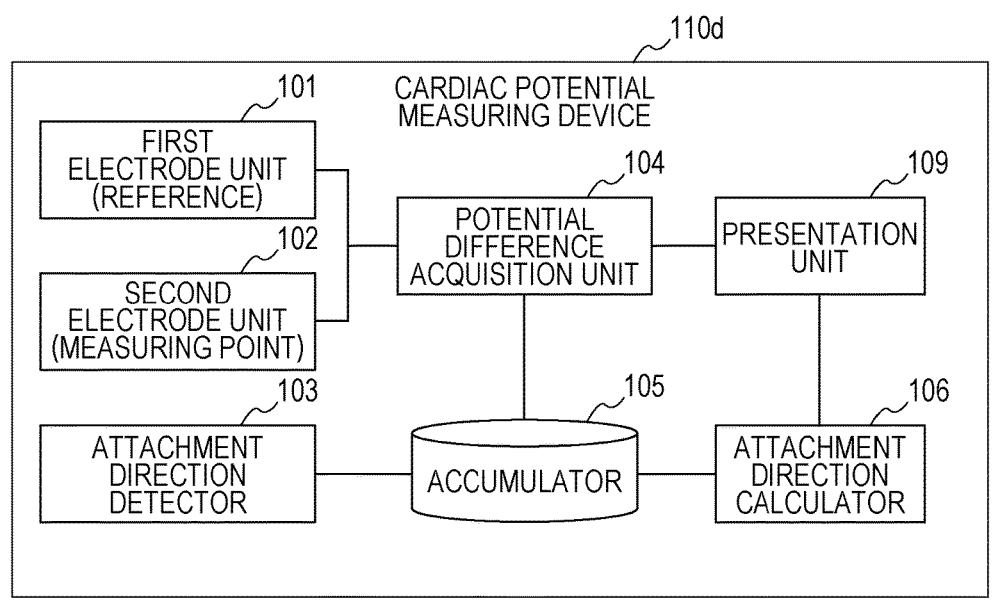
FIG. 25 is a block diagram illustrating a configuration of the cardiac potential measuring device including a presentation unit.

FIG. 25 is a block diagram illustrating a configuration of cardiac potential measuring device 110d including presentation unit 109. Cardiac potential measuring device 110d includes first electrode 101, second electrode unit 102, attachment direction detector 103, potential difference acquisition unit 104, accumulator 105, attachment direction calculator 106, and presentation unit 109. Different from cardiac potential measuring device 110a of the first exemplary embodiment, cardiac potential measuring device 110d presents various information items such as the preferred attachment direction calculated by attachment direction calculator 106 via presentation unit 109 included in cardiac potential measuring device 110d itself. It is applicable not only to the first exemplary embodiment but also to the second and third exemplary embodiments that the cardiac potential measuring device may include presentation unit 109.

Physical structures of the cardiac potential measuring device according to the present disclosure can be implemented in various forms. The various structures of the cardiac potential measuring device according to the present disclosure will be described below.

Figure 26A:
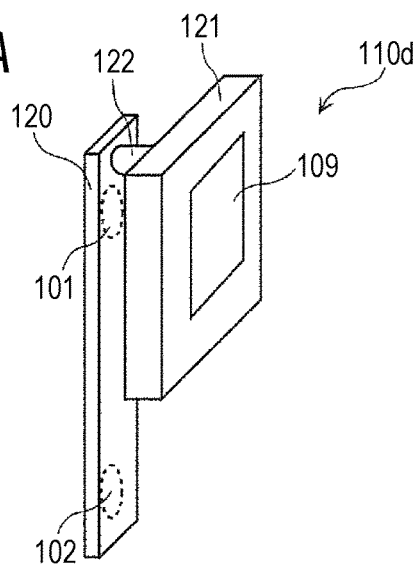
FIG. 26A is a diagram illustrating an example of an external appearance of the cardiac potential measuring device including the presentation unit.
Figure 26B:
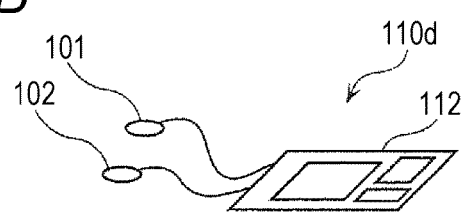
FIG. 26B is a diagram illustrating an example of a circuit module that embodies the cardiac potential measuring device including the presentation unit.
Figure 26C:
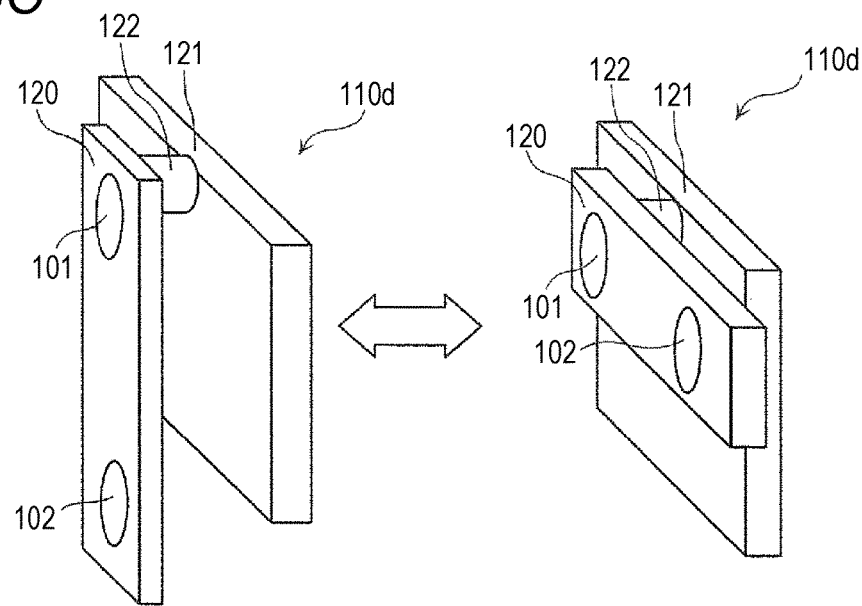
FIG. 26C is a diagram illustrating an example of use of the cardiac potential measuring device including the presentation unit.

FIG. 26A to FIG. 26C are diagrams illustrating examples of specific structures of cardiac potential measuring device 110d including the presentation unit illustrated in FIG. 25. FIG. 26A is a diagram illustrating an example of external appearance (structure) of cardiac potential measuring device 110d including presentation unit 109. Cardiac potential measuring device 110d includes plate 120 for holding at least one of first electrode 101 and second electrode unit 102, locking piece 121 to be locked to the body of the user or clothes that wrap the body of the user, and support 122 for holding plate 120 and locking piece 121 spaced by a certain distance and for holding plate 120 pivotably in a plane of plate 120. In the present exemplary embodiment, plate 120 holds first electrode 101 and second electrode unit 102 so that first electrode 101 and second electrode unit 102 may be spaced by a certain distance in plan view of plate 120. FIG. 26B, which is similar to FIG. 2A, is a diagram illustrating an example of a circuit module that embodies cardiac potential measuring device 110d. Here, respective components of cardiac potential measuring device 110d are mounted on processing substrate 112 connected to first electrode 101 and second electrode unit 102 via lead wires. FIG. 26C is a diagram illustrating an example of use of cardiac potential measuring device 110d. Cardiac potential measuring device 110d has a mechanism that allows second electrode unit 102 to rotate around first electrode 101 by including plate 120, locking piece 121, and support 122 that holds plate 120 and locking piece 121 pivotably. In addition, presentation unit 109 is provided on an opposite side of the electrodes (first electrode 101 and second electrode unit 102).

Figure 27:
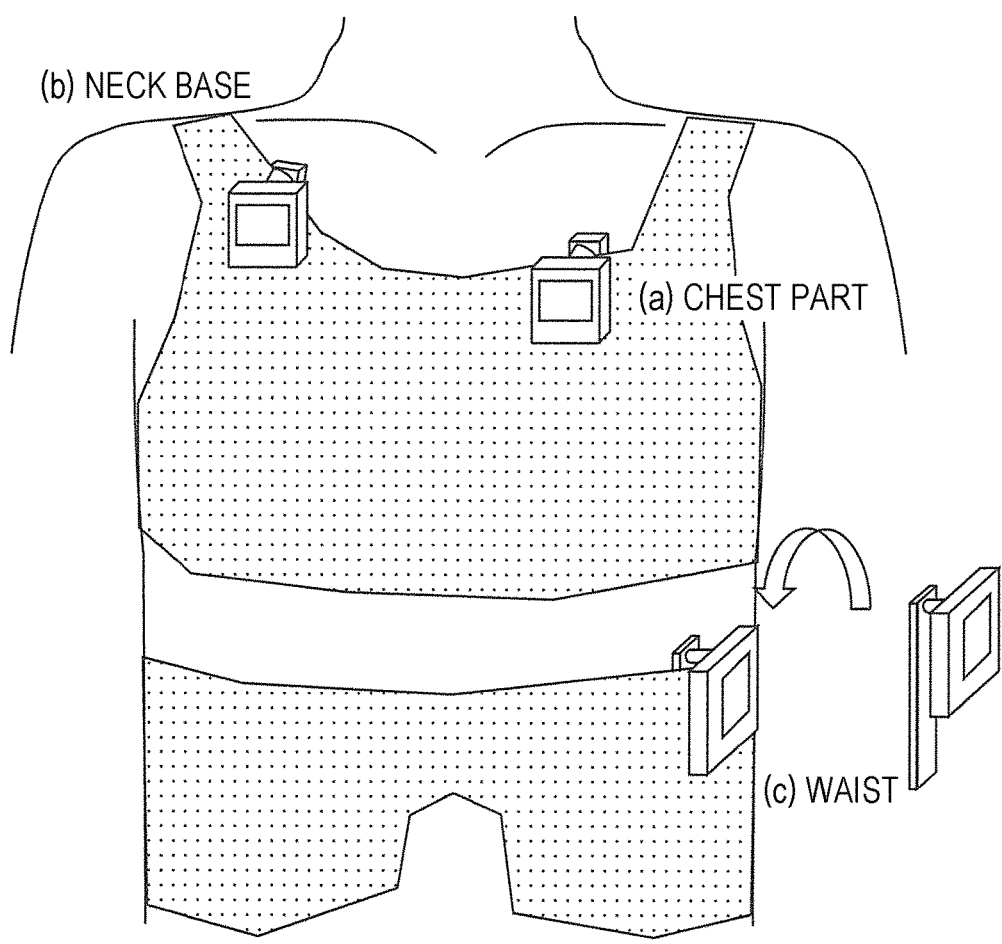
FIG. 27 is a diagram illustrating an example of attachment of the cardiac potential measuring device including the presentation unit.

FIG. 27 is a diagram illustrating an example of attachment of cardiac potential measuring device 110d including the presentation unit illustrated in FIG. 26A. Cardiac potential measuring device 110d can be attached to a chest part ((a) of FIG. 27), neck base ((b) of FIG. 27), or waist ((c) of FIG. 27), for example, in a form of nipping a shirt or underwear. Presentation unit 109 is disposed on a front side (a side facing outward from the body of the user). First electrode 101 and second electrode unit 102 disposed on a back side (a side contacting the body of the user) come in contact with skin of the user, which enables measurement of cardiac potential. The user can measure in the first attachment state and the second attachment state, for example, while checking information via presentation unit 109. In addition, the above-described rotating mechanism prevents first electrode 101 that serves as reference from deviating significantly between the first attachment state and the second attachment state, and enables more precise calculation of the preferred attachment direction.

Figure 28A:
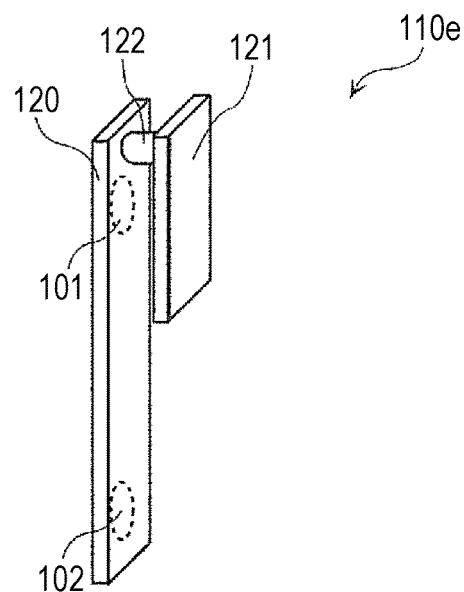
FIG. 28A is an external appearance diagram of a clip type cardiac potential measuring device.
Figure 28B:
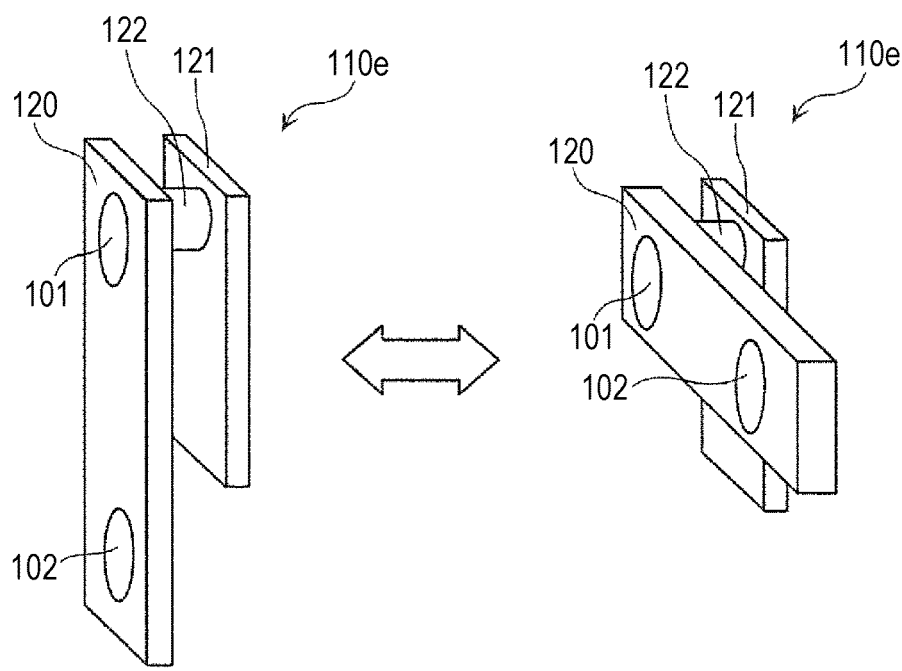
FIG. 28B is a diagram illustrating an example of use of the clip type cardiac potential measuring device.

As illustrated in an external appearance (structure) diagram of FIG. 28A, as a specific example of implementation of cardiac potential measuring devices 110a to 110c that do not include the presentation unit according to the first to third exemplary embodiments described above, the cardiac potential measuring device may be implemented as clip type cardiac potential measuring device 110e, which may implement cardiac potential measuring device 110e including the rotating mechanism. FIG. 28B is a diagram illustrating an example of use of clip type cardiac potential measuring device 110e. A method for attachment is similar to the example of attachment illustrated in FIG. 27. For example, cardiac potential measuring device 110e is attached in the form of nipping a shirt or underwear. First electrode 101 and second electrode unit 102 disposed on the back side come in contact with skin of the user, which enables measurement of cardiac potential. In addition, cardiac potential measuring device 110e includes the rotating mechanism, which prevents first electrode 101 that serves as reference from deviating significantly between the first attachment state and the second attachment state, and enables more precise calculation of the preferred attachment direction, in a similar manner to cardiac potential measuring device 110d illustrated in FIG. 26A.

Figure 29A:
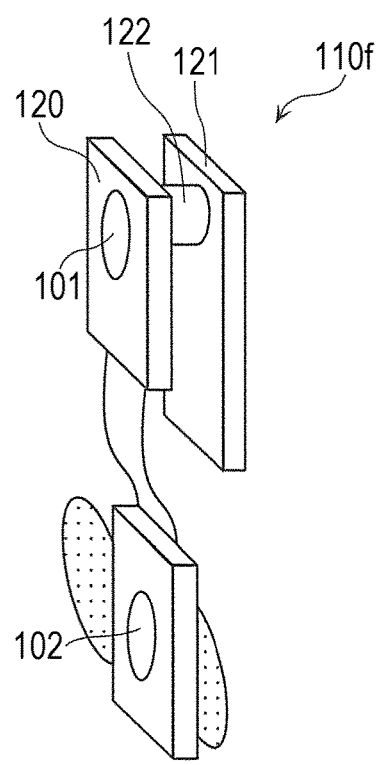
FIGS. 29A to 29B are external appearance diagrams of the cardiac potential measuring device including the clip type first electrode and a patch type second electrode unit.
Figure 29B:
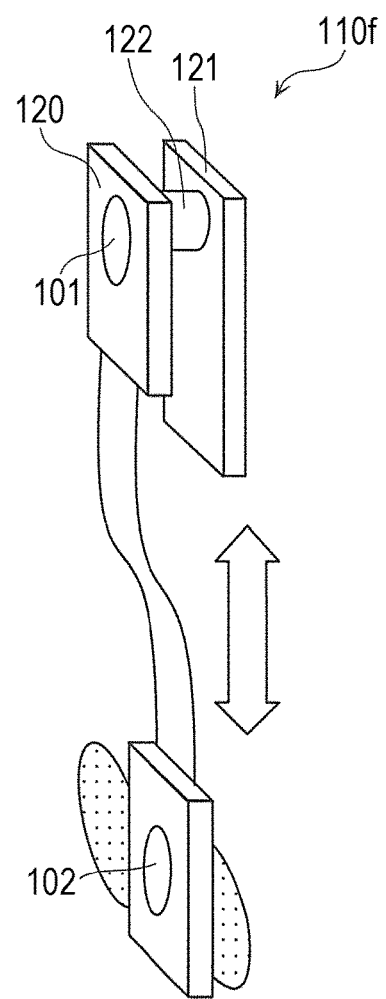

As illustrated in the external appearance (structure) diagrams of FIGS. 29A to 29B, the cardiac potential measuring device according to the present disclosure may be implemented as cardiac potential measuring device 110f that includes clip type first electrode 101, patch type second electrode unit 102, and the above-described rotating mechanism. Patch type second electrode unit 102 has a structure in which the electrode is formed on a pad that can be stuck on the body. Cardiac potential measuring device 110f having such a structure enables adjustment of the attachment direction because the clip (plate 120, locking piece 121, and support 122) nips and fixes first electrode 101 that serves as reference with clothing, and second electrode unit 102 is rotated and attached.

Moreover, a length between the electrodes (between first electrode 101 and second electrode unit 102) may be fixed as illustrated in FIG. 29A, and may be adjustable as illustrated in FIG. 29B. In a form illustrated in FIG. 29A, first electrode 101 and second electrode unit 102 are connected with a band made of resin or the like, for example. In a form illustrated in FIG. 29B, first electrode 101 and second electrode unit 102 are connected with an elastic band made of cloth or the like, for example. Since measurement of cardiac potential is measurement of potential differences, larger potential difference may occur as the distance between the electrodes increases depending on a position, which may increase immunity to a noise. Therefore, as illustrated in FIG. 29B, a mechanism for adjusting the length between the electrodes will enable measurement in accordance with daily noise environments. In calculation of the preferred attachment direction, the length between the electrodes is preferably identical during measurement in the first attachment state and the second attachment state. Meanwhile, providing a sensor or the like for detecting the length between the electrodes enables calculation of the preferred attachment direction even if the length between the electrodes differs. This is because it is possible to calculate the preferred attachment direction by making addition in consideration of the length between the electrodes when the above-described vector addition is made.

Figure 30A:
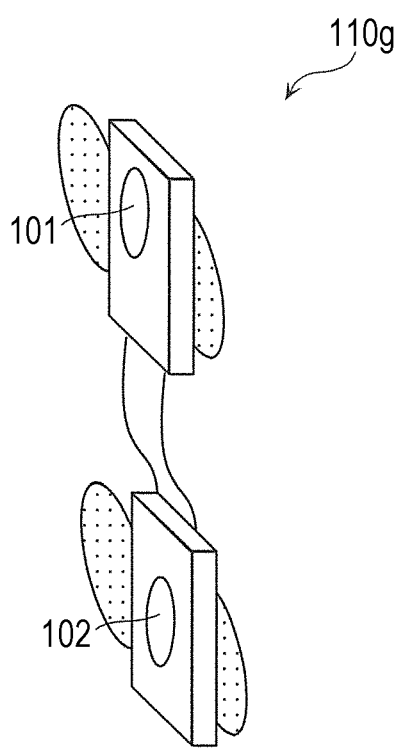
FIGS. 30A to 30B are external appearance diagrams of the cardiac potential measuring device including the clip type first electrode and the clip type second electrode unit.
Figure 30B:
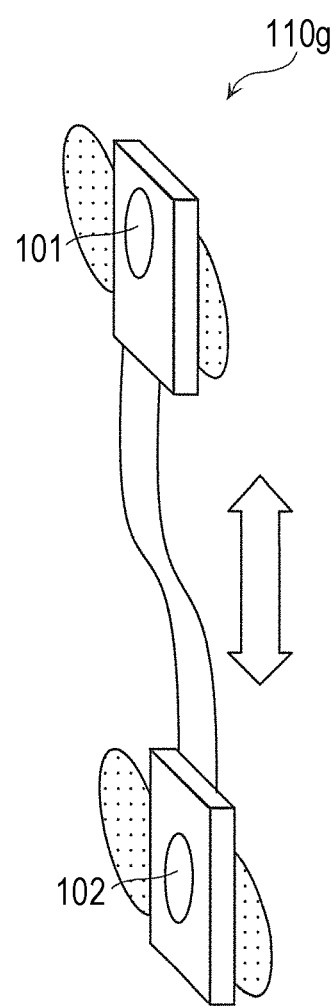

In addition, the mechanism for adjusting the length between first electrode 101 and second electrode unit 102 is not necessarily limited to the clip type, and both electrodes may be patch type. FIGS. 30A to 30B are external appearance (structure) diagrams of cardiac potential measuring device 110g with first electrode 101 and second electrode unit 102 being configured as patch type. The length between the electrodes is fixed in a form illustrated in FIG. 30A, and is adjustable in a form illustrated in FIG. 30B. In the form illustrated in FIG. 30B, adjustment of the length in accordance with the position of measurement enables measurement of larger potential differences.

Figure 31A:
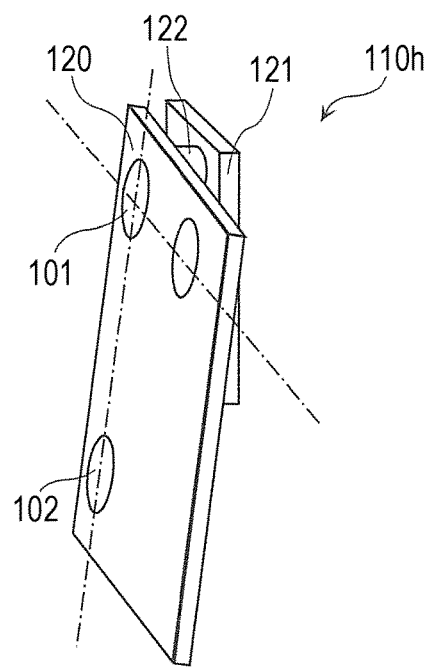
FIGS. 31A to 31B are external appearance diagrams of the cardiac potential measuring device including three electrodes.
Figure 31B:
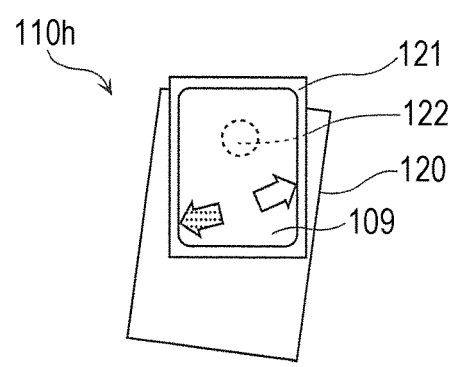

In addition, the cardiac potential measuring device according to the present disclosure may be implemented as cardiac potential measuring device 110h having plate 120 provided with three electrodes (first electrode 101, second electrode unit 102, and third electrode unit 123), as illustrated in the external appearance (structure) diagrams of FIGS. 31A to 31B. FIG. 31A is an external appearance (structure) diagram of clip type cardiac potential measuring device 110h including three electrodes viewed from plate 120. FIG. 31B is an external appearance (structure) diagram of cardiac potential measuring device 110h viewed from locking piece 121.

As illustrated in FIG. 31A, in cardiac potential measuring device 110h, plate 120 is provided with first electrode 101, second electrode unit 102, and third electrode unit 123 that are attached to the body of the user. First electrode 101, second electrode unit 102, and third electrode unit 123 are held on plate 120 so that a direction of a virtual line that connects first electrode 101 and second electrode unit 102 may be orthogonal to a direction of a virtual line that connects first electrode 101 and third electrode unit 123. The term "orthogonal" may include not only a case where the virtual lines cross at an angle of 90 degrees but also a case where the virtual lines cross generally at an angle of 90 degrees (for example, from 80 degrees to 100 degrees). According to such a structure, the potential difference between a pair of first electrode 101 and second electrode unit 102 is acquired by potential difference acquisition unit 104 as a first potential difference, and the direction of the virtual line that connects first electrode 101 and second electrode unit 102 is detected by attachment direction detector 103 as a first attachment direction. At the same time, the potential difference between a pair of first electrode 101 and third electrode unit 123 is acquired by potential difference acquisition unit 104 as a second potential difference, and the direction of the virtual line that connects first electrode 101 and third electrode unit 123 is detected by attachment direction detector 103 as a second attachment direction.

In addition, as illustrated in FIG. 31B, in cardiac potential measuring device 110h, presentation unit 109 may be provided in locking piece 121, and various information items may be presented via presentation unit 109. For example, as illustrated in FIG. 31B, a more preferable attachment direction may be presented via presentation unit 109 based on the preferred attachment direction calculated by attachment direction calculator 106.

While the cardiac potential measuring device and the cardiac potential measuring method according to the present disclosure have been described above in accordance with the first to third exemplary embodiments, the variations, and the structure examples, the present disclosure is not limited to these exemplary embodiments, variations, and structure examples. Exemplary embodiments in which various modifications conceivable by a person skilled in the art are made and exemplary embodiments that are made by combining components of different exemplary embodiments may also be within the scope of one or more aspects of the present disclosure, as long as such exemplary embodiments do not depart from the spirit of the present disclosure.

For example, the present disclosure also includes a cardiac potential measuring device including all features (attachment direction calculator 106, attachment direction check unit 201, and attachment position check unit 202) of cardiac potential measuring devices 110a to 110c in the above-described first to third exemplary embodiments.

The structures of the cardiac potential measuring devices illustrated in FIG. 26 to FIG. 31 may be applied to any one of cardiac potential measuring devices 110a to 110d in the above exemplary embodiments.

In each of the above exemplary embodiments, each component may be configured of dedicated hardware or may be implemented by execution of a software program suitable for each component. Each component may be implemented by a program executing unit, such as a CPU or a processor, reading and executing the software program recorded in a recording medium, such as a hard disk drive or a semiconductor memory. The software for implementing the cardiac potential measuring device of each of the exemplary embodiments or the like is the following program.

That is, this program causes a computer to execute a first step to a fourth step below. The first step is a step of acquiring, by potential difference acquisition unit 104, the first potential difference that is the potential difference between first electrode 101 and second electrode unit 102 as cardiac potential in a case where first electrode 101 and second electrode unit 102 are attached to the body in the first attachment state.

The second step is a step of acquiring, by potential difference acquisition unit 104, the second potential difference that is the potential difference between first electrode 101 and second electrode unit 102 as cardiac potential in a case where first electrode 101 and second electrode unit 102 are attached to the body in the second attachment state.

When the direction of the virtual line that connects first electrode 101 and second electrode unit 102 attached to the body is defined as the attachment direction, the third step is a step of detecting the first attachment direction that is the attachment direction detected by attachment direction detector 103 in the first attachment state, and the second attachment direction that is the attachment direction detected by attachment direction detector 103 in the second attachment state, or an angle made by the first attachment direction and the second attachment direction.

The fourth step is a step of calculating and outputting the preferred attachment direction that is the attachment direction in which the potential difference larger than any one of the first potential difference and the second potential difference is generated, based on the first potential difference acquired in the first step, the second potential difference acquired in the second step, and the first attachment direction and the second attachment direction detected in the third step, or the angle.

The present disclosure may be implemented by transmission of the above-described computer program or digital signal via electric telecommunication lines, wireless or wired communication lines, a network such as, typically, the Internet, or the like.

The present disclosure may be a computer system including a microprocessor and a memory, the memory may store the computer program, and the microprocessor may operate in accordance with the computer program.

The present disclosure may be implemented by another independent computer system through recording of the above program or digital signal in the recording medium and transportation, or through transportation of the above program or digital signal via the network or the like.

Furthermore, each of the exemplary embodiments and the variations may be combined with one another.

In the present disclosure, all or part of the units and devices, or all or part of functional blocks in the block diagrams illustrated in FIG. 1, FIG. 14, and FIG. 20 may be executed by one or more electronic circuits including a semiconductor device, a semiconductor integrated circuit (IC), or an LSI (Large Scale Integration). The LSI or IC may be integrated into one chip, and may be constituted through combination of two or more chips. For example, functional blocks other than a storage element may be integrated into one chip. The integrated circuit that is called LSI or IC here is also called differently depending on degree of integration, and may be called a system LSI, VLSI (Very Large Scale Integration), or ULSI (Ultra Large Scale Integration). An FPGA (Field Programmable Gate Array) that is programmed after manufacture of the LSI, or a reconfigurable logic device that allows reconfiguration of connection inside the LSI or setup of circuit blocks inside the LSI can be used for an identical purpose. Furthermore, all or part of functions or operations of units, devices, or part of the devices can be executed by software processing. In this case, the software is recorded in non-temporary recording media, such as one or more ROMs, optical disks, or hard disk drives. When the software is executed by a processor, the software causes the processor and a peripheral device to execute a specific function within the software. The system or device may include the one or more non-temporary recording media that record the software, the processor, and necessary hardware devices, for example, an interface.

The exemplary embodiments disclosed this time are to be considered in all respects as illustrative and not restrictive. The scope of the present disclosure is indicated by the appended claims rather than by the foregoing description. All changes which come within the meaning and range of equivalency of the claims are therefore intended to be embraced therein.

The present disclosure can be used as a cardiac potential measuring device or a cardiac potential measuring system, in particular, as a cardiac potential measuring device or the like with which general users who are not specialists in cardiac potential measurement can measure cardiac potential simply while leading daily life.

REFERENCE SINGS LIST 101 first electrode
102 second electrode unit
103 attachment direction detector
104 potential difference acquisition unit
105 accumulator
106 attachment direction calculator
107 transmitter
108 receiver
109 presentation unit
110a to 110h cardiac potential measuring device
111 terminal device
112 processing substrate
120 plate
121 locking piece
122 support
123 third electrode unit
201 attachment direction check unit
202 attachment position check unit

What is claimed is:

1. A cardiac potential measuring device comprising:
a first electrode and a second electrode;
a potential difference acquisition circuitry that acquires a potential difference between the first electrode and the second electrode as cardiac potential;
an attachment direction detector that detects an attachment direction that is a direction of a virtual line that connects the first electrode and the second electrode attached to the body of the user; and
an attachment direction calculator that calculates and outputs a preferred attachment direction in which the potential difference larger than any one of a first potential difference and a second potential difference is generated, based on:
(a) the first potential difference acquired by the potential difference acquisition circuitry when the first electrode and the second electrode are attached to the body of the user in a first attachment state;
(b) the second potential difference acquired by the potential difference acquisition circuitry when the first electrode and the second electrode are attached to the body of the user in a second attachment state; and
(c) a first attachment direction detected in the first attachment state, and a second attachment direction in the second attachment state, or an angle made by the first attachment direction and the second attachment direction.

2. The cardiac potential measuring device according to claim 1, wherein the attachment direction calculator calculates a direction in which a maximum potential gradient is generated from a vector specified by the first potential difference and the first attachment direction, and a vector specified by the second potential difference and the second attachment direction, and outputs the direction as the preferred attachment direction.

3. The cardiac potential measuring device according to claim 1, further comprising a display unit configured to display the preferred attachment direction that is output from the attachment direction calculator.

4. The cardiac potential measuring device according to claim 1, further comprising:
an attachment position check circuitry that determines whether a distance between a position of the first electrode in the first attachment state and a position of the first electrode in the second attachment state is within a predetermined range,
wherein the attachment direction calculator calculates and outputs the preferred attachment direction when the attachment position check circuitry determines that the distance between the position of the first electrode in the first attachment state and the position of the first electrode unit in the second attachment state is within the predetermined range.

5. The cardiac potential measuring device according to claim 1, further comprising:
   a plate comprising at least one of the first electrode and the second electrode;
   a locking piece to be locked to the body or to clothes worn on the body of the user; and
   a support positioned between the plate and the locking piece, the support holding the plate pivotally in a plane of the plate.

6. The cardiac potential measuring device according to claim 5, wherein
   the plate comprises the first electrode and the second electrode, and
   the first electrode and the second electrode are spaced by a certain distance in plain view of the plate.

7. The cardiac potential measuring device according to claim 6, wherein
   the plate comprises the first electrode, the second electrode, and a third electrode to be attached to the body, and
   the first electrode, the second electrode, and the third electrode are positioned on the plate so that the direction of the virtual line that connects the first electrode and the second electrode may be orthogonal to a direction of a virtual line that connects the first electrode and the third electrode.

8. A method for measuring cardiac potential comprising:
   acquiring a first potential difference between a first electrode and a second electrode attached to a body of the user in a first attachment state;
   detecting a first attachment direction that is a direction of a virtual line that connects the first electrode and the second electrode attached to the body of the user in a first attachment state;
   acquiring a second potential difference between the first electrode and the second electrode attached to the body of the user in a second attachment state;
   detecting a second attachment direction that is a direction of a virtual line that connects the first electrode and the second electrode attached to the body of the user in a second attachment state; and
   calculating and outputting a preferred attachment direction in which the potential difference larger than any one of the first potential difference and the second potential difference is generated, based on (a) the first potential difference, (b) the second potential difference, and (c) a first attachment direction, and a second attachment direction in the second attachment state, or an angle made by the first attachment direction and the second attachment direction.

* * * * *